US006544792B1

(12) United States Patent
Diaz-Torres

(10) Patent No.: US 6,544,792 B1
(45) Date of Patent: Apr. 8, 2003

(54) PRODUCTION OF SECRETED POLYPEPTIDES

(75) Inventor: Maria R. Diaz-Torres, Los Gatos, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/595,386

(22) Filed: Jun. 14, 2000

Related U.S. Application Data

(63) Continuation of application No. PCT/US99/31010, filed on Dec. 21, 1999.

(51) Int. Cl.$^7$ .......................... C12P 21/00; C12P 21/04; C12N 1/21; C12N 1/20; C12N 9/00

(52) U.S. Cl. ............... 435/691; 435/252.3; 435/252.31; 435/71.1; 435/183

(58) Field of Search .............................. 435/69.1, 252.3, 435/252.31, 183, 71.1

(56) References Cited

U.S. PATENT DOCUMENTS

| | | | |
|---|---|---|---|
| 3,817,837 A | 6/1974 | Rubenstein | 435/7.9 |
| 3,850,752 A | 11/1974 | Wilhelmus | 435/7.93 |
| 3,939,350 A | 2/1976 | Kronick | 250/362 |
| 3,996,345 A | 12/1976 | Ullman | 436/537 |
| 4,275,149 A | 6/1981 | Litman | 435/7.91 |
| 4,277,437 A | 7/1981 | Maggio | 422/61 |
| 4,366,241 A | 12/1982 | Tom | 435/7.91 |
| 4,816,567 A | 3/1989 | Cabilly | 530/387.3 |
| 5,264,366 A | 11/1993 | Ferrari et al. | 435/252.31 |

FOREIGN PATENT DOCUMENTS

| | | |
|---|---|---|
| WO | WO 88/06623 | 9/1988 |
| WO | WO 97/33551 | 9/1997 |
| WO | WO 98/11203 A1 | 3/1998 |
| WO | WO 99/27107 A2 | 6/1999 |
| WO | WO 00/39323 A2 | 7/2000 |

OTHER PUBLICATIONS

Bork , Genome Research, 10:348–400, 2000.*
Broun et al. , Science 282:1315–1317, 1998.*
Van de Loo et al. , Proc. Natl. Acad. Sci. 92:6743–6747, 1995.*
Abouhamad et al., "Peptide transport and chemotaxis in *Escherichia coli* and *Salmonella typhimurium*: characterization of the dipeptide permease (Dpp) and the dipeptide–binding protein" (1991) *Mol. Microbiol.* vol. 5, No. 5, pp. 1035–1047.
Abouhamad et al., "The dipeptide permease of *Escherichia coli* closely resembles other bacterial transport systems and shows growth–phrase–dependent expression" (1994) *Mol. Microbiol.* vol. 14, No. 5, pp. 1077–1092.

Alloing, G. et al., "Three Highly Homologous Membrane–bound Lipoproteins Participate in Oligopeptide Transport by the Ami System of the Gram–positive *Streptococcus pneumoniae*" (1994) *J. Mol. Biol.* 241(1): 44–58.
Altschul et al., "Basic Local Alignment Search Tool" (1990) *J. Mol. Biol.* 215, 403–410.
Altschul et al., "Local Alignment Statistics" (1996) *Methods in Enzymology*, vol. 266, pp. 460–480.
Anthony, C. The Biochemistry of Methylotrophs (1982) pp. 207.
Ausubel et al., Short Protocols in Molecular Biology (1992) pp. 2–28–2–41.
Bakhiet, N. et al., "Studies on transfection and transformation of protoplasts of Bacillus larvae, *Bacillus subtilis* and *Bacillus popilliae*" (1985) *Appl. Environ. Microbiol.* vol. 49, No. 3, pp. 577–581.
Ballance, D. J. et al., "Transformation of *Aspergillus Nidulans* by the Orotidine–5'–Phosphate Decarboxylase Gene of *Neurospora Crassa*" (1983) *Biochem Biophys. Res. Commun.* vol. 112, No. 1, pp. 284–289.
Batzer, M. et al., "Enhanced evolutionary PCR using oligonucleotides with inosine at the 3'–terminus" (1991) *Nucleic Acid Res.* vol. 19, No. 18, p. 5081.
Bolhuis, A. et al., "*Bacillus subtilis* can modulate its capacity and specificity for protein secretion through temporally controlled expression of the sips gene for signal peptidase I" (1996) *Mol. Microbiol.* vol. 22, No. 4, pp. 605–618.
Borezee, E. et al., "OppA of *Listeria monocytogenes*, an Oligopeptide–Binding Protein Required for Bacterial Growth at Low Temperature and Involved in Intracellular Survival" (2000) *Infect. And Immun.* vol. 68, No. 12, pp. 7069–7077.
Bruinenberg, P. et al., "Proteinase overproduction in *Lactococcus lactis* strains: regulation and effect on growth and acidification in milk" (1992) *Appl. Environ. Microbiol.* vol. 58, No. 1, pp. 78–84.
Bull, et al., (1984) *Nature* 310, 701–704.
Cassol, S. et al., "Rapid DNA fingerprinting to control for specimen errors in HIV testing by the polymerase chain reaction" (1992) *Mol. And Cellular Probes* 6, 327–331.
Cassol, S. et al., "Stability of Dried Blood Spot Specimens for Protection of Human Immunodeficiency Virus DNA by Polymerase Chain Reaction" (1992) *J. Clin. Microbiol.* vol. 30, No. 12, pp. 3039–3042.
Chan, E. et al., "Ribonucleoprotein SS–B/La belongs to a protein family with consensus sequences for RNA–binding" (1989) *Nucleic Acid Research* vol. 17, No. 6, pp. 2233–2244.

(List continued on next page.)

Primary Examiner—Rebecca E. Prouty
Assistant Examiner—Delia M. Ramirez
(74) *Attorney, Agent, or Firm*—Genencor International, Inc.

(57) ABSTRACT

Described herein are methods and compositions for the production and secretion of polypeptides. Included herein is the use of interrupting peptide transport activity for an increase in polypeptide production and/or secretion.

17 Claims, 4 Drawing Sheets

OTHER PUBLICATIONS

Chang, S. et al., "High Frequency Transformation of *Bacillus subtilis* Protoplasts by Plasmid DNA" (1979) *Mol. Gen. Genet* 168, 111–115.

Claverie–Martin, F. et al., "Analysis of the altered mRNA Stability (ams) Gene from *Escherichia colil*" (1991) *J. Biol. Chem.* vol. 266, No. 5, pp. 2843–2851.

Contente et al., "Marker Rescue Transformation by Liner Plasmid DNA in *bacillus subtilis*" (1979) *Plasmid* 2:555–571.

Cosby W.M. et al., "Altered srf Expression in *Bacillus subtilis* Resulting from Changes in Culture pH is Dependent on the Spo0k Oligopeptide Permease and the Com QX System of Extracellular Control" (1998) *J. Bacteriol* vol. 180, No. 6, pp. 1438–1445.

Detmers, F. et al., "Kinetics and Specificity of peptide Uptake by the Oligopeptide Transport System of *Lactococcus lactis*" (1998) *Biochem.* vol. 37, pp. 16671–16679.

Deuerling, E. et al., "The ftsH gene of *Bacillus subtilis* is involved in major cellular processes such as sporulation, stress adaptation and secretion" (1997) *Mol. Microbiol.* vol. 23, No. 5, pp. 921–933.

Devereux, J. et al., "A comprehensive set of sequence analysis programs for the VAX" (1984) *Nucl. Acid Res.* vol. 12, No. 1, pp. 387–395.

Dunny and Leonard, "Cell–cell communication in Gram–positive bacteria" (1997) *Ann. Rev. Microbiol.* 51:527–564.

Eijsink, V. et al., "Induction of bacteriocin production in *Lactobacillus sake* by a secreted peptide" (1996) *J. Bacteriol.* vol. 178m No. 8.

Estell, D.V. et al., "Engineering an Enzyme by Site–directed Mutagenesis to Be Resistant to Chemical Oxidation" (1985) *J. Biol. Chem,* vol. 260, No. 11, pp. 6518–6521.

Fang, G. et al., "Manipulation of activity and orientation of membrane–reconstituted di–tripeptide transport protein DtpT of *Lactococcus lactis*" (1999) Mol. Memb. Biol. 16, 297–304.

Feng, D. et al., "Progressive Sequence Alignment as a prerequisite to Correct Phylogenetic Trees" (1987) *J. Mol. Evol.* 25:351–360.

Fischer, H. et al., "Introduction of plasmid pC194 into *Bacillus thuringiensis* by protoplast transformation and plasmid transfer" (1984) *Arch. Microbiol.* 139:213–217.

Fisher, S. et al., "Control of Carbon and Nitrogen Metabolism in *Bacillus subtilis*" (1991) *Annu. Rev. Microbiol.* 45:107–35.

Foucaud, C. et al., "Specificity of Peptide Transport Systems in *Lactococcus lactis*: Evidence for a Third System which Transports Hydrophobic Di– and Tripeptides" (1995) *J. of Bacteriol.* vol. 177, No. 16, pp. 4652–4657.

Gibson et al., "Genetic Characterization and Molecular Cloning of the Tripeptide Permease (tpp) Genes of *Salmonella typhimurium*" (1984) *J. Bacteriol.* vol. 160, No. 1, pp. 122–130.

Guyer et al., "Purification and Characterization of a Periplasmic Oligopeptide Binding Protein from *Escherichia coli*" (1985) *J. Biol. Chem.* vol. 260, No. 19, pp. 10812–10818.

Hagege, J., et al., "A developmentally regulated Streptomyces endoribonuclease resembles ribonuclease E of *Escherichia coli*" (1997) *Mol. Microbiol.* vol. 25, No. 6, pp. 1077–1090.

Hagting, A. et al., "Amplified expression, purification and functional reconstitution of the dipeptide and tripeptide transport protein of *Lactococcus lactis*" (1997) *Eur. J. Biochem.* vol. 247, pp. 581–587.

Hagting, A. et al., "Membrane Topology of the Di– and Tripeptide Transport Protein of *Lactococcus lactis*" (1997) *Biochemistry* vol. 36, pp. 6777–6785.

Hagting, A. et al., "The Di–and Tripeptide Protein of *Lactococcus lactis,*" (1994) *J. Biol. Chem.* vol. 269, No. 15, pp. 11391–11399.

Haima et al., "Novel plasmid market rescue transformation system for molecular cloning in *Bacillus subtilis* enabling direct selection of recombinants" (1990) *Mol. Gen. Genet.* 223:185–191.

He, X. et al., "The protease genes of *Bacillus subtilis*" (1991) *Res. Microbiol.* 142, 797–803.

Henkin, T.M. et al., "Catabolite repression of alpha–amylase gene expression in *Bacillus subtilis* involves a trans–acting gene product homologous to the *Escherichia coli* lacI and galR repressors" (1991) *Mol Microbiol.* vol. 5, No. 3, pp. 575–584.

Higgins & Sharp, "Fast and sensitive multiple sequence alignments on a microcomputer" (1989) *CABIOS* vol. 5, No. 2, pp. 151–153.

Higgins, C. "ABC Transporters: From Microorganisms to Man" (1992) *Annu. Rev. Cell Biol.* 8:67–113.

Higgins, C. "The ABC of Channel Regulation" (1995) *Cell* vol. 82, 693–696.

Hiles et al., "Molecular Characterization of the Oligopeptide Permease of *Salmonella typhimurium*" (1987) *J. Mol. Biol.* 195:125–142.

Houbova, et al., "Transfer of Liposome–Encapsulated Plasmid DNA to *Bacillus subtilis* Protoplasts and Calcium–Treated *Escherichia coli* Cells" (1985) *Folia Microbiol.* 30, 97–100.

John, M. A. et al., "Transformation of *Aspergillus nidulans* using the argB gene" (1984) *Enzyme Microb Technol.* vol. 6, pp. 386–389.

Johnstone, I. L. et al., "Cloning an *Aspergillus nidulans* developmental gene by transformation" (1985) *EMBO* vol. 4, No. 5, pp. 1307–1311.

Karlin et al., "Applications and statistics for multiple high–scoring segments in molecular sequences" (1993) *PNAS USA* vol. 90, pp. 5873–5787.

Kawarabayasi, Y. "Complete Sequence and Gene Organization of the Genome of a Hyper–thermophilic Archaebaterium" *DNA Res.* 5 (2), 55–76 (1998).

Kelly, J. M. et al., "Transformation of *Aspergillus niger* by the amdS gene of *Aspergillus nidulans*" (1985) *EMBO* vol. 4, No. 2, pp. 475–479.

Kinsey, et al., "Transformation of *Neurospora crassa* with the Cloned am (Glutamate Dehydrogenase) Gene," (1984) *Molecular and Cellular Biology* vol. 4, No. 1, pp. 117–122.

Klier, A. et al., "Positive Regulation in the Gram–Positive Bacterium: *Bacillus subtilis*" (1992) *Annu. Rev. Microbiol.* 46:429–459.

Koide A. et al., "Identification of a second oligopeptide transport system in *Bacillus subtilis* and determination of its role in sporulation" (1994) *Mol. Microbiol.* 13(3):417–426.

Kroll, D.J. et al., "A Multifunctional Prokaryotic Protein Expression System: Overproduction, Affinity Purification, and Selective Detection" (1993) *DNA and Cell Biol.* vol. 12, No. 5, pp. 441–453.

Kunji, E. et al., "The proteolytic systems of lactic acid bacteria" (1996) Antonie Van Leeuwenhoek, vol. 70, No. 2–4, pp. 187–221. Review.

Kunji, E. et al., "Transport of beta–casein–derived peptides by the oligopeptide transport system is a crucial step in the proteolytic pathway of *Lactococcus lactis*" (1995) *J. Biol. Chem.* vol. 270, No. 4, pp. 1569–1574.

Lazazzera, B. et al., "An Autoregulatory Circuit Affecting Peptide Signaling in *Bacillus subtilis*" (1999) *J. of Bacteriol.* vol. 181, No. 17, pp. 5193–5200.

Lazazzera, B. et al., "An Exported Peptide Functions Intracellularly to Contribute to Cell Density Signaling in *B. subtilis*" (1997) *Cell* 89, 917–925.

Lazazzera, B. et al., "The ins and outs of peptide signaling" (1998) *Trends in Microbiol* vol. 6, No. 7, pp. 288–294.

LeDeaux, J. R. et al., "Analysis of non–polar deletion mutations in the genes of the spoo0K (opp) operon of *Bacillus subtilii*" (1997) *FEMS Microbiology Letters* 153: 63–69.

Leonard B.A.B. et al., "Enterococcus faecalis pheromone binding protein, PrgZ, recruits a chromosomal oligopeptide permease system to import sex pheromone cCF10 for induction of conjugation" (1996) Proc. Natl. Acad. Sci. USA. Jan. 9;93(1):260–4.

Leskelä S. et al., "Molecular analysis of an operon in *Bacillus subtilis* encoding a novel ABC transporter with a role in exoprotein production, sporulation and competence" (1996) *Microbiology,* 142, 71–77.

Leskelä, S. et al., "Ecs, an ABC transporter of *Bacillus subtilis* : dual signal transduction functions affecting expression of secreted proteins as well as their secretion" (1999) *Mol. Microbiol.* vol. 31, No. 2, pp. 533–544.

Lin–Chao, S. et al., "The Rate of Processing and Degradation of Antisense RNAI Regulates the Replication of ColE1–Type Plasmids in Vivo" (1991) *Cell* vol. 65, pp. 1233–1242.

Lin–Chao, S. et al., "Effects of Nucleotide Sequence on the specificity of me–dependent and Rnase E–mediated Cleavages of RNA I Encoded by the pBR322 Plasmid" (1994) *J. Biol. Chem.* vol. 269, No. 14, pp. 0797–10803.

Lu, Biqing, et al., "Expression of the tpr protease gene of *Porphyromonas gingivalis* is regulated by peptide nutrients" (1998) *Infect. Immun.* vol. 66, No. 11, pp. 5147–5156.

Maddox D.E. et al., "Elevated Serum Levels in Human Pregnancy of a Molecule Immonochemically Similar to Eosinophil Granule Major Basic Protein" (1983) *J. Exp. Med.* (1983) vol. 158, pp. 1211–1226.

Magnuson, R. et al., "Biochemical and Genetic Characterization of a Competence Pheromone from *B. subtilis*" (1994) *Cell* vol. 77, 207–216.

Maniatis et al., *Molecular Cloning: A Laboratory Manual* (1982) pp. 382–389.

Mann et al., "Transformation of Bacillus supp.: an Examination of the Transformation of Bacillus Protoplasts by Plasmids pUB110 and pHV33" (1986) *Current Microbiol.* vol. 13, pp. 191–195.

Marugg, J. et al., "Identical Transcriptional Control of the divergently Transcribed prP and prtM Genes that Are Required for Proteinase Production in *Lactococcus lactis* SK11" (1996) *J. Bacteriol.* vol. 178, No. 6, pp. 1525–1531.

Marugg, J. et al., "Medium–Dependent Regulation of Proteinase Gene Expression in *Lactococcus lactis:* Control of Transcription Initiation by Specific Dipeptides" (1995) *J. of Bacteriol.* vol. 177, No. 11, pp. 2982–2989.

Mathiopoulos, C. et al., "Identification of *Bacillus subtilis* genes expressed early during sporulation" (1989) *Mol. Microbiol.* vol. 3, No. 8, pp. 1071–1081.

McDonald, et al., "Plasmid Transformation of *Bacillus sphaericus* 1593" (1984) *J. Gen. Microbiol.* 203–208.

Mierau, I. et al., "Multiple–Peptidase Mutants of *Lactococcus lactis* Are Severely Impaired in Their Ability to Grow in Milk" (1996) *J. of Bacteriol.* vol. 178, No. 10, pp. 2794–2803.

Msadek, T. et al., "Signal transduction pathway controlling synthesis of a class of degradative enzymes in *Bacillus subtilis:* Expression of the regulatory genes and analysis of mutations in degS and degU." *J. Bacteriol.* vol. 172, No. 2, pp. 824–834.

Msadek, T. et al., (1993) "Two component regulatory systems" In A. L. Sonenshein, J. A. Hoch, and R. Losick (Ed.), *Bacillus subtilis and other gram–positive bacteria.* American Society for Microbiology, Washington, D. C., pp. 729–745.

Msadek, T., "When the going gets tough: survival strategies and environmental signaling networks in *Bacillus subtilis*" *Trends Microbiol.* 7:201–207.

Mullaney, E.J. et al., "Primary structure of the trpC gene from *Aspergillus nidulans*" (1985) *MGG* vol. 199, pp. 37–45.

Nakajima, H. et al., "Cloning and Functional Expression in *Escherichis coli* of the Gene Encoding the Di– and Tripeptide Transport Protein of *Lactobacillus helveticus*" (1997) *App. And Environ. Microbiol.* vol. 63, No. 6, pp. 2213–2217.

Neddleman & Wunsch, "A General Method Applicable to the Search for Similarities in the Amino Acid Sequence of Two Proteins" (1970) *J. Mol. Biol.* 48, 443–453.

Nicholson, Wayne L. et al., "Effect of decoyinine on the regulation of alpha–amylase synthesis in *Bacillus subtilis*" (1987) *J. Bacteriol.* vol. 169, No. 12, pp. 5867–5869.

Nodwell, J.R. et al., "An oligopeptide permease responsible for the import of an extracellular signal governing aerial mycelium formation in *Streptomyces coelicolor*" (1996) *Mol. Microbiol.* vol. 22, No. 5, pp. 881–893.

Ohtsuka et al., "An Alternative Approach to Deoxyoligonucleotides as Hybridization Probes by Insertion of Deoxyinosine at Ambiguous Codon Positions" (1985) *J. Biol. Chem.* vol. 260, No. 5, pp. 2605–2608.

Olson et al., "Identification and Characterization of dppA, an *Escherichia coli* Gene Encloding a Periplasmic Dipeptide Transport Protein" (1991) *J. Bacteriol* 173:234–244.

Payne, J. et al., "Peptide Transport by Micro–organisms" (1994) *Adv. In Microbiol. Physiol.* vol. 36, pp. 1–80.

Pearson, W. et al., "Improved tools for biological sequence comparison" (1988) *PNAS USA* vol. 85, pp. 2444.

Perego et al., "The oligopeptide transport system of *Bacillus subtilis* plays a role in the initiation of sporulation" (1991) I. 5:173–185.

Perego, M. et al., "Aspartyl phosphate phosphatases deactivate the response regulator components of the sporulation signal transduction system in *Bacillus subtilis*" (1996) *Mol Microbiol.* 19:1151–1157.

Perego, M. et al., "Cell–cell communication regulates the effects of protein aspartate phosphatases on the phosphorelay controlling development in *Bacillus subtilis*" (1996) *Proc. Natl. Acad. Sci. USA* 93:1549–1553.

Perego, M. et al., "Multiple protein–aspartate phosphatases provide a mechanism for the integration of diverse signals in the control of development in *B. subtilis*" (1994) *Cell* 79:1047–1055.

Perego, M., "A peptide export–import control circuit modulating bacterial development regulates protein phosphatases of the phosphorelay" (1997) *Proc. Natl. Acad. Sci. USA* 94:8612–8617.

Podbielski, A. et al., "Novel series of plasmid vectors for gene inactivation and expression analysis in group A streptococci (GAS)" (1996) *Gene* 177:137–147.

Podbielski, J. et al., "Cysteine protease SpeB expression in group A streptococci is influenced by the nutritional environment but SpeB does not contribute to obtaining essential nutrients" (1999) *Med. Microbiol. Immunol.* 188: 99–109.

Porath, J. "Immobilized Metal Ion Affinity Chromatography" (1992) 3:263–281.

Rossi, J. "Making ribozymes work in cells" (1994) *Current Biology*, vol. 4, No. 5, pp. 469–471.

Rossolini et al., "Use of deoxyinosine–containing primers vs degenerate primers for polymerase chain reaction based on ambiguous sequence information" (1994) *Mol Cell. Probes* 8, 91–98.

Roy, M.K. et al., "Purification and Properties of Ribonuclease E, an RNA–Processing Enzyme from *Escherichia Coli*" (1983) *Biochim. Biophys. Acta* 747, 200–208.

Rudner, D. Z. et al., "The spo0K Locus of *Bacillus subtilis* Is Homologous to the Oligopeptide Permease Locus and Is Required for Sporulation and Competence" *J. Bacteriol.* vol. 173, No. 4, pp. 1388–1398.

Serror, P.A. et al., "Interaction of Cod, a novel *Bacillus subtilis* DNA–binding protein, with the dpp promoter region" (1996) *J. Mol. Microbiol.* 20:843–852.

Slack, F. et al., "A gene required for nutritional repression of the *Bacillus subtilis* dipeptide permease operon" (1995) *Mol. Microbiol.* vol. 15, No. 4, pp. 689–702.

Slack, F. et al., "Mutations that relieve nutritional repression of the *Bacillus subtilis* dipeptide permease operon" (1993) *J Bacteriol.* vol. 175, No. 15, pp. 4605–4614.

Smith & Waterman, "Comparison of Biosequences" (1981) *Adv. Appl. Math.* 2, 482–489.

Smith et al., "Protoplast Transformation in Coryneform Bacteria and Introduction of an α–Amylase Gene from *Bacillus amyloliquefaciens* into *Brevibacterium lactofermentum*" (1986) *Appl. And En. Microbiol.* 51:634.

Stein and Cohen, "Oligodeoxynucleotides as Inhibitors of Gene Expression: A Review" (1988) *Cancer Res.* 48, 2659–2668.

Steiner, H. Y. et al., "The PRT family: a new group of peptide transporters" (1995) *J. Mol. Microbiol.* 16:825–834.

Tam, R. et al., "Structural, Functional, and Evolutionary Relationships among Extracellular Solute–Binding Receptors of Bacteria" (1993) *Microbiol. Rev.* vol. 57, No. 2, pp. 320–346.

Tame, J. et al., "The Structural Basis of Sequence–Independent Peptide Binding by OppA Protein" (1994) *Science* vol. 264, pp. 1578–1581.

Tilburn et al., "Transformation by integration in *Aspergillus nidulans*" (1982) *Gene* 26, 205–221.

Tomcsanyi, et al., "Processing Enzyme Ribonuclease E Specifically Cleaves RNA I—An Inhibitor of Primer Formation in Plasmid DNA Synthesis" (1985) *J. Mol. Biol.* 185, 713–720.

Tynkkynen et al., "Genetic and Biochemical Characterization of the Oligopeptide Transport System of *Lactococcus lactis*" (1993) *J. of Bacteriol.* vol. 175, No. 23, pp. 7523–7532.

Valle, F. et al., "Subtilisin: a Redundantly Temporally Regulated Gene?" I. Smith, R. A. Slepecki, and P. Setlow (ed), *Regulation of Prokaryotic Development*, American Society for Microbiology, Washington, D. C., pp. 131–146.

Van der Krol et al., "Modulation of Eukaryotic Gene Expression by Complementary RNA or DNA Sequences" (1988) *Bio. Tech.* vol. 6, No. 10, pp. 958–976.

Vorobjeva et al., "Transformation of *Bacillus Megaterium* Protoplasts by Plasmid DNA" (1980) *FEMS Microbiol. Letters* 7 pp. 261–263.

Ward (1983) "Proteinases in Microbiol Enzymes and Biotechnology" *Applied Science* pp. 251–317.

Walter, "Method with Haemaglobin, Casein and Azocoll as Substrate," *Methods of Enzymatic Analysis*, $3^{rd}$ ed. V. 5.

Mathlopoulos et al., "A *Bacillus subtilis* dipeptide transport system expressed early during sporulation," Molecular Microbiology, 5(8): 1903–1913 (1991).

Podbleiski et al., "Molecular characterization of group A streptococcal (GAS) oligopeptide permease (Opp) and its effect on cysteine protease production," Molecular Microbiology, 21(5): 1087–1099 (1996).

Podbleiski et al., "The group A streptococcal dipeptide permease (Dpp) is involved in the uptake of essential amino acids and affects the expression of cysteine protease," Molecular Microbiology, 28(6): 1323–1334 (1998).

Slack et al., "Transcriptional regulation of a *Bacillus subtilis* dipeptide transport operon," Molecular Microbiology, 5(8): 1915–1925 (1991).

Copy of International Search Report for PCT/US00/16764.

Mathiopoulos et al., "A *Bacillus subtilis* dipeptide transport system expressed early during sporulation," Mol. Microbio. (1991) 5(8), 1903–1913 (XP–000982568).

Slack et al., "Transcriptional regulation of a *Bacillus subtilis* dipeptide transport operon," Mol. Microbio. (1991) 5(8), 1915–1925 (XP–000982589).

Podbielski et al., "Molecular characterization of a group A streptococcal (GAS) oligopeptide permease (Opp) and its effect on cysteine protease production," Mol. Microbio. (1996) 21(5), 1087–1099 (XP–000906862).

Podbielski et al., "The group A streptococcal dipeptide permease (Dpp) is involved in the uptake of essential amino acids and affects the expression of cysteine protease," Mol. Microbio. (1998) 28(6), 1323–1334 (XP–000906863).

* cited by examiner 1 ccggacgttt ttgatgaggt atttgaaaga accctgagaa aatatgaact gcttacagaa
61 caggttggta aacaaacatg aatccttgaa agaggattct ttttatca ctgaatgatt
121 gagattttc ccagttatat tgcatttttc ctcttttttt aatataattt gttagaatat
181 tcataattta gtaaaaaagg aggagcgtt a tgaaattgta catgtcagta gatatggaag
241 gtatttcggg tcttccggac gataccttg tggattccgg caagcggaat tatgaacgcg
301 gacggcttat catgactgaa gaagcaaact actgtattgc tgaagcgttt aacagcgggt
361 gtaccgaggt gctggtcaat gacagtcatt cgaagatgaa taatctgatg gttgaaaagc
421 ttcaccctga agcagacttg attctggtg acgtcaaacc attttcaatg gtggagggac
481 tggatgatac gttagaggc gctttgtttc tcggttatca tgcgagagcc tcgactcctg
541 gtgtcatgtc acacagcatg attttcggcg tccgtcattt ttacataaac gatcggcctg
601 tcggtgagct tggattaaat gcatacgttg ccggttatta tgatgtcccg gtattaatgg
661 tagccgggga tgaccggcgcg gcgaaggaag cagaagagct tatcccgaac gtgacgacag
721 ccgcagtcaa acaaaccatt tcaagatccg cagtgaagtg cttgtcgcct gcgaaagccg
781 gacggctgtt gacagaaaaa acgccatttg ccctgcaaaa caaggacaaa gtcaagccgc
841 tcacaccgcc tgacaggcca gttctgagca ttgaattcgc caattatggc caagcagaat
901 gggcgaatct gatgccggga acggaaatca agacgggaac tacaaccgtt caatttcagg
961 cgaaggacat gcttgaagcc tatcaggcga tgcttgtcat gactgagctt gcgatgcgga
1021 catcattctg ctaa aggggt gtttaggct ttggcgcgat acatgataaa gcgttttgg
1081 gcaatggcag ctacgatttt ggtgattacc accctgactt tgttctcat gaaggtcatt
1141 cccggatctc cttttaacga ggagagaggc acaaatgaag ccgttcaaaa aaatctcgaa
1201 gcctactatc acttagacga tcctctcatt ttccaataca ttttctactt aaaatccatc
1261 attacattcg atttcggacc ttcaattaaa aaaccgtcgg acagcgtaaa tgatatgctg
1321 gaacgcggat ttcccgtttc ctttgagctt gggatgacag cgattgtcat tgctgtgatt
1381 tctgggctgg tgctgggcgt aatcgctgca ctccgccgca atggcttttt ggactacgcc
1441 gcgatgagtc ttgcagtact cggcatctcc atcccgaatt ttattctggc aacattgctc
1501 attcagcaat tgctgtcaa tctcaaacta tttcccgctg cgacatggac gagcccgatt
1561 catatggtgc ttccgaccgc agcgcttgct gtagggccaa tggcgatcat tgccaggctg
1621 acacggtcga gcatggtcga agttctgaca caggattata tccgcacagc aaaagcaaaa
1681 gggctttctc cgttcaaaat tatcgtaaaa cacgcactca gaaatgcact catgcccgtc
1741 attaccgtcc tgggcacact cgtcgccagc atcttaacag gaagctttgt cattgaaaaa
1801 atctttgcca ttccgggaat gggaaaatat tttgttgaaa gcattaatca gcgggactac
1861 cccgtgatta tgggaacgac cgttttttac agcgtcattc tgattatcat gctgtttttg
1921 gtcgatttgg cctacggtct cttagacccg cgcattaaac tgcataagaa agggtgaagc
1981 gtgtgaatct ccctgtacaa acgatgaac gccagccaga acagcacaat caggtgcctg
2041 atgagtggtt tgtcttgaat caggaaaaaa atcgggaagc cgattcggtc aagcggccga
2101 gtttgtcata cacgcaggat gcctggagga ggctgaaaaa aaataaatta gcgatggccg
2161 gactcttat tcttttattt cttttttgtca tggcagttat cgggccctt ttatcgcccc
2221 atagtgtcgt acgccaatcg ctgacagaac aaaatcttcc gccctcagcc gatcattggt
2281 tcgcaccga tgaactcggc cgggatgtgt tacccgaac atggtatggc gcgagaatct
2341 cgttgtttgt cggcgtgatg gcagcactga ttgattttt gatcggtgtc atttacggag
2401 gcgttgccgg ctataaaggc ggcaggattg acagcattat gatgcggatt atcgaagtgc
2461 tgtacggact gccgtatctg cttgttgtca tttgctgat ggtgctcatg gaccgggac
2521 tgggcacgat tattgtggcg ctgactgtga ccgggtggt cggcatggcg agaattgtaa
2581 gaggccaggt gcttcagatt aaaaattatg aatatgtact cgcctcgaaa acctttggcg
2641 cgaaaaccctt tcgcatcatc cggaagaatt tgctgcgcaa tactatggga gcgatcatcg
2701 tacaaatgac attaaccgta cctgccgcca tattcgcaga atcattttta agctttctcg
2761 gcctgggcat acaggctccg tttgcaagtt ggggcgtgat ggcgaatgac ggcctgccta
2821 cgattttatc tgggcattgg tggcgcctgt ttttccggc cttttcata tcttcgacga
2881 tgtacgcgtt taatgtgctg ggggacggat tgcaggatgc gcttgaccct aagctgagga
2941 ggtgactgta tggaaaaagt tctgtcagtc caaaatctgc acgtgtcttt tacgacttac
3001 ggcgggacgg ttcaggcggt cagaggggtg agctttgatt tgtataaagg agaaacccttt

FIGURE 1A

```
3061 gcgatcgtcg gcgaatccgg ctgcggcaaa agcgttacct cccaaagcat catgggcctg
3121 cttccgcctt attcggcgaa ggtgacagac ggcaggattc tatttaaaaa caaagacctt
3181 tgccgtctct ctgacaaaga aatgagaggt ataaggggag ccgacatttc tatgattttt
3241 caagacccga tgacggcgtt aaaccctacg ctgactgtcg gcgaccagct gggggaagcg
3301 ctattgcgcc acaaaaaaat gagcaaaaaa gcggcacgga aagaggtgct ttccatgctg
3361 tcattggttg gtattccaga tcccggagag cgcctaaagc aatatcccca ccaattcagc
3421 ggcggtatga gacagcggat tgtcattgcg atggcgctga tttgcgagcc tgatatctta
3481 attgcggatg aaccgaccac cgccctggat gtaaccattc aggcacagat tttagagctg
3541 tttaaagaga ttcagagaaa aacgatgtg tctgtcattc tgattacgca cgatttaggg
3601 gttgttgccc aggtagctga cagagtcgca gtcatgtatg ccggaaaat ggcggaaatc
3661 ggcacaagaa aagatatttt ttatcagccg cagcacccat atacaaaagg cctgctgggc
3721 tctgtcccgc ggctggattt aaatggcgct gagctgaccc cgattgacgg aacgccgccg
3781 gatttatttt cgcctccgcc gggctgcccg tttgccgccc gctgtccgaa caggatggtt
3841 gtgtgtgaca gggtgtaccc gggccagacg atcagatctg actcgcacac cgtcaactgc
3901 tggctgcagg atcaacgagc agagcatgcg gtgctgtcag gagatgcgaa ggattgaaca
3961 tgaaagggg gaagagg atg aaacgagtga aaaagctatg gggcatgggt cttgcattag
4021 gactttcgtt tgcgctgatg gggtgcacag caaatgaaca ggccggaaaa gaaggcagtc
4081 atgataaggc aaaaaccagc ggagaaaagg tgctgtatgt aaataatgaa atgaaccga
4141 cttcattcga tccgccgatc ggctttaata atgtgtcatg gcagccgtta aataacatca
4201 tggagggct gacgcgtctt ggcaaagatc atgagcccga gccggcaatg gcggagaaat
4261 ggtctgtttc gaaagataat aaaaacttaca catttacgat tcgggaaaat gcgaaatgga
4321 caaacggaga tcctgtaaca gccggagact tcgaatacgc gtggaagcgg atgcttgatc
4381 cgaaaaaagg cgcttcatcg gcattcctag gttatttat tgaaggcggc gaagcatata
4441 acagcgggaa agggaaaaaa gacgatgtga aggtgacggc aaaggatgat cgaacccttg
4501 aagttacact ggaagcaccg caaaaatatt tcctgagcgt tgtgtccaat cccgcgtatt
4561 tcccggtaaa tgaaaaggtc gataaagaca atccaaagtg gtttgctgag tcggatacat
4621 ttgtcggaaa cggcccgttt aagctgacgg aatggaagca tgatgacagc atcacaatgg
4681 agaaaagcga cacgtattgg gataaggata cagtgaagct tgataaggtg aaatgggcga
4741 tggtcagtga cagaaataca gattaccaga tgtttcaatc aggggaactt gataccgctt
4801 atgtccctgc tgagctgagt gatcagctgc ttgatcagga taacgtcaat attgttgacc
4861 aggcggtct ctatttctat cgatttaatg tcaacatgga gccgttccaa aatgaaaaca
4921 tcagaaaagc ctttgcgatg gctgtggatc aagaggaaat tgtaaagtac gtcacgaaaa
4981 ataatgaaaa accggcgcac gcctttgtat cgcctgggtt tacgcagcct gacggcaaag
5041 attccgtga agcaggcgga gacctgatca agcctaacga aagcaaagcg aagcagctgc
5101 tcgaaaaggg catgaaggaa gaaaactata ataagcttcc tgcgatcacg cttacttaca
5161 gcacaaagcc ggagcataaa aagattgccg aagctattca gcaaaaattg aaaaatagcc
5221 ttggagtcga tgtgaagctg gccaatatgg aatggaacgt attttagag gatcaaaaag
5281 cgctgaaatt ccaattctct caaagctcat ttttgcctga ttatgcagac cctatcagtt
5341 ttctggaagc ctttcaaacg ggaaattcga tgaaccgcac aggctgggcc aataaagaat
5401 acgatcagct gatcaaacag gcgaaaaacg aagccgatga aaaaacacgg ttctctctta
5461 tgcatcaagc tgaagagctg ctcatcaatg aagcgccgat cattccggtt tattttata
5521 atcaggttca cctgcaaaat gaacaagtaa aaggaattgt ccgtcaccct gtcggctata
5581 tcgatttaaa atgggcagat aaaaaactga t ggaggcgatt gaggaaatac tgcttcttta
5641 tgcgaaggag cggtattttt tctctttctt gcacgtatac gtagggtgca gagcaaatga
5701 aaggagtgtt ttcgttgaat tacaagccga aagcgttgaa caagggtgat acagtcggag
5761 tgatcgcgcc cgcaagtccg ccggatccaa aaaagctt
```

FIGURE 1B

MKLYMSVDMEGISGLPDDTFVDSGKRNYERGRLIMTEEANYCIA
EAFNSGCTEVLVNDSHSKMNNLMVEKLHPEADLISGDVKPFSMVEGLDDTFRGALFLG
YHARASTPGVMSHSMIFGVRHFYINDRPVGELGLNAYVAGYYDVPVLMVAGDDRAAKE
AEELIPNVTTAAVKQTISRSAVKCLSPAKAGRLLTEKTPFALQNKDKVKPLTPPDRPV
LSIEFANYGQAEWANLMPGTEIKTGTTTVQFQAKDMLEAYQAMLVMTELAMRTSFC

FIGURE 2

MARYMIKRFWAMAATILVITTLTFVLMKVIPGSPFNEERGTNEA
VQKNLEAYYHLDDPLIFQYIFYLKSIITFDFGPSIKKPSDSVNDMLERGFPVSFELGM
TAIVIAVISGLVLGVIAALRRNGFLDYAAMSLAVLGISIPNFILATLLIQQFAVNLKL
FPAATWTSPIHMVLPTAALAVGPMAIIARLTRSSMVEVLTQDYIRTAKAKGLSPFKII
VKHALRNALMPVITVLGTLVASILTGSFVIEKIFAIPGMGKYFVESINQRDYPVIMGT
TVFYSVILIIMLFLVDLAYGLLDPRIKLHKKG

FIGURE 3

MNLPVQTDERQPEQHNQVPDEWFVLNQEKNREADSVKRPSLSYT
QDAWRRLKKNKLAMAGLFILLFLFVMAVIGPFLSPHSVVRQSLTEQNLPPSADHWFGT
DELGRDVFTRTWYGARISLFVGVMAALIDFLIGVIYGGVAGYKGGRIDSIMMRIIEVL
YGLPYLLVVILLMVLMGPGLGTIIVALTVTGWVGMARIVRGQVLQIKNYEYVLASKTF
GAKTFRIIRKNLLRNTMGAIIVQMTLTVPAAIFAESFLSFLGLGIQAPFASWGVMAND
GLPTILSGHWWRLFFPAFFISSTMYAFNVLGDGLQDALDPKLRR

FIGURE 4

MEKVLSVQNLHVSFTTYGGTVQAVRGVSFDLYKGETFAIVGESG
CGKSVTSQSIMGLLPPYSAKVTDGRILFKNKDLCRLSDKEMRGIRGADISMIFQDPMT
ALNPTLTVGDQLGEALLRHKKMSKKAARKEVLSMLSLVGIPDPGERLKQYPHQFSGGM
RQRIVIAMALICEPDILIADEPTTALDVTIQAQILELFKEIQRKTDVSVILITHDLGV
VAQVADRVAVMYAGKMAEIGTRKDIFYQPQHPYTKGLLGSVPRLDLNGAELTPIDGTP
PDLFSPPPGCPFAARCPNRMVVCDRVYPGQTIRSDSHTVNCWLQDQRAEHAVLSGDAKD

FIGURE 5

MKRVKKLWGMGLALGLSFALMGCTANEQAGKEGSHDKAKTSGEKVLYVNNENEPTSFDPPI
GFNNVSWQPLNNIMEGLTRLGKDHEPEPAMAEKWSVSKDNK
TYTFTIRENAKWTNGDPVTAGDFEYAWKRMLDPKKGASSAFLGYFIEGGEAYNSGKGK
KDDVKVTAKDDRTLEVTLEAPQKYFLSVVSNPAYFPVNEKVDKDNPKWFAESDTFVGN
GPFKLTEWKHDDSITMEKSDTYWDKDTVKLDKVKWAMVSDRNTDYQMFQSGELDTAYVPAELSDQL
LDQDNVNIVDQAGLYFYRFNVNMEPFQNENIRKAFAMAVDQEEIVKYVTK
NNEKPAHAFVSPGFTQPDGKDFREAGGDLIKPNESKAKQLLEKGMKEENYNKLPAITL
TYSTKPEHKKIAEAIQQKLKNSLGVDVKLANMEWNVFLEDQKALKFQFSQSSFLPDYA
DPISFLEAFQTGNSMNRTGWANKEYDQLIKQAKNEADEKTRFSLMHQAEELLINEAPI
IPVYFYNQVHLQNEQVKGIVRHPVGYIDLKWADKN

FIGURE 6

PRODUCTION OF SECRETED POLYPEPTIDES

RELATED APPLICATIONS

The present application is a continuation to PCT/US99/31010 filed Dec. 21, 1999, incorporated herein in its entirety.

FIELD OF THE INVENTION

The present invention relates to the increased production of proteins, preferably, heterologous secreted proteins and cells having interrupted peptide transport activity.

BACKGROUND

Secretion of heterologous polypeptides is a widely used technique in industry. A cell can be transformed with a nucleic acid encoding a heterologous polypeptide of interest to be secreted and thereby produce large quantities of desired polypeptides. This technique can be used to produce a vast amount of polypeptide over what would be produced naturally. Polypeptides of interest have a number of industrial applications, including therapeutic and agricultural uses, as well as use in foods, cosmetics, cleaning compositions, animal feed, etc.

Thus, increasing secretion of polypeptides is of interest. Secretion of polypeptides into periplasmic space or into their culture media is subject to a variety of parameters. Typically, vectors for secretion of a polypeptide of interest are engineered to position DNA encoding a secretory signal sequence 5' to the DNA encoding the DNA of interest.

Attempts to increase secretion have often fallen into one of the following three areas: trying several different signal sequences, mutating the signal sequence, and altering the secretory pathway within the host. While some success has been found with the above methods, generally, they are time consuming and novel methods are desirable. Therefore, a problem to be solved is how to produce and/or secrete more proteins without solely relying on altering the signal sequence.

The instant invention provides a novel approach to improving secretion of polypeptides in a cell. Also provided herein are novel compositions useful in the methods of polypeptide secretion provided herein, and methods of making such compositions.

SUMMARY OF THE INVENTION

In one aspect of the invention, a method of increasing secretion of a polypeptide in a cell is provided. In a preferred embodiment, said cell selected would express at least one peptide transport protein. In one embodiment, the method comprises inactivating said at least one peptide transport protein in said cell and culturing said cell under conditions suitable for expression and secretion of said polypeptide.

The methods provided herein are applicable for production or secretion of polypeptides in a variety of cell types. For example, the cell can be selected from the group consisting of a plant cell, a fungal cell, a gram-negative microorganism and a gram-positive microorganism. In one embodiment, said cell is a gram-negative microorganism, preferably, a member of the family Escherichia. In another embodiment, said cell is a gram-positive microorganism, preferably a member of the family Bacillus. In a preferred embodiment, said cell is a gram-positive microorganism and is a member of the family Bacillus wherein said member of the family Bacillus is selected from the group consisting of B. licheniformis, B. lentus, B. brevis, B. stearothermophilus, B. alkalophilus, B. amyloliquefaciens, B. coagulans, B. circulans, B. lautus, B. thuringiensis, B. methanolicus and B. anthracis.

The polypeptide which is secreted or produced by the methods provided herein can be any polypeptide. In a preferred embodiment, it is a heterologous polypeptide. In one aspect, the polypeptide is selected from the group consisting of hormone, enzyme, growth factor and cytokine. In one embodiment, the polypeptide is an enzyme, preferably selected from the group consisting of proteases, carbohydrases, reductases, lipases, isomerases, transferases, kinases, phophatases, cellulase, endo-glucosidase H, oxidase, alpha-amylase, glucoamylase, lignocellulose hemicellulase, pectinase and ligninase. In one aspect, said polypeptide is a bacillus protease, preferably subtilisin. In another aspect, said polypeptide is an amylase, preferably, bacillus amylase.

The peptide transport protein can be a variety of proteins and can be inactivated in a variety of ways. In one aspect, the peptide transport protein is a gene product of a dciA operon, and preferably, is the gene product of the dciAE gene. The protein can be inactivated at the protein or nucleic acid level. In one aspect, the protein is inactivated because the gene encoding said protein has been mutated. In another embodiment, the operon comprising said gene has been mutated. The mutation can be caused in a variety of ways including one or more frameshifts, insertions, substitutions and deletions, or combinations thereof. The deletion can be of a single nucleotide or more, including deletion of the entire gene.

In another aspect of the invention, a method for producing a polypeptide in a cell is provided which comprises the steps of obtaining a cell comprising nucleic acid encoding a polypeptide to be produced, said cell further comprising a peptide transport operon wherein at least one gene product of said operon is inactive in said cell, and culturing said cell under conditions suitable for expression such that said polypeptide is produced. Preferably, the peptide transport operon is a dciA operon. The gene product of said operon can be inactivated at the nucleic acid or protein level. Preferably, the inactivated gene product is encoded by dciAA or dciAE.

In another aspect of the invention provided herein is a cell comprising a peptide transport operon, wherein said operon has been mutated such that said cell has increased polypeptide secretion. In a preferred embodiment, said operon is a dciA operon. In one embodiment, said operon has been mutated to inactivate a gene product of a dciAA and/or dciAE gene.

BRIEF DESCRIPTION OF THE DRAWINGS

FIGS. 1A and 1B show an embodiment of a nucleic acid (SEQ ID NO:1) encoding a dciA operon, wherein the nucleotides encoding dciAA and dciAE are shown, respectively, underlined and in bold.

FIG. 2 shows an embodiment of an amino acid sequence for dciAA (SEQ ID NO: 2), encoded by nucleotides 210–1034 of the nucleic acid sequence shown in FIGS. 1A and 1B, wherein the amino acids shown in underlined are omitted in an embodiment of inactive dciAA provided herein.

FIG. 3 shows an embodiment of an amino acid sequence for dciAB (SEQ ID NO: 3), encoded by nucleotides 1051–1977 of the nucleic acid sequence shown in FIGS. 1A and 1B.

FIG. 4 shows an embodiment of an amino acid sequence for dciAC (SEQ ID NO: 4), encoded by nucleotides 1983–2945 of the nucleic acid sequence shown in FIGS. 1A and 1B.

FIG. 5 shows an embodiment of an amino acid sequence for dciAD (SEQ ID NO: 5), encoded by nucleotides 2950–3957 of the nucleic acid sequence shown in FIGS. 1A and 1B.

FIG. 6 shows an embodiment of an amino acid sequence for dciAE (SEQ ID NO: 6), encoded by nucleotides 3978–5609 of the nucleic acid sequence shown in FIGS. 1A and 1B, wherein the amino acids shown in underlined are omitted in an embodiment of inactive dciAA provided herein.

DETAILED DESCRIPTION OF THE INVENTION

In one aspect of the invention, a method of increasing production and/or secretion of a polypeptide in a cell is provided. In a preferred embodiment, said cell selected for said method expresses at least one peptide transport protein. Preferably, the cell selected endogenously expresses said peptide transport protein, however, the cell can be transformed to express said protein. In one embodiment, the method comprises inactivating at least one peptide transport protein in said cell. The method further comprises culturing said cell under conditions suitable for expression and secretion of said polypeptide.

"Peptide transport protein" as used herein refers to a protein involved in peptide transport. Proteins involved in peptide transport are considered to have peptide transport activity. In one embodiment, a peptide transport protein includes a protein involved in dipeptide or oligopeptide transport, preferably dipeptide transport. In one embodiment, the peptides which are transported by the peptide transport proteins or systems described herein include peptides which are 2–10 amino acids long, preferably 2–8, and more preferably 2–6. In a preferred embodiment, oligopeptides are 3–7 amino acids long, preferably 5 or 6 amino acids long and dipeptides are two amino acids.

The peptide transport protein which is inactivated is preferably involved in the import of proteins. As further discussed below, inactivation can occur in a variety of ways and by individual mutations or combinations of mutations. Peptide transport systems can include activity in exporting and/or importing peptides. In a preferred embodiment herein, peptide transport activity is interrupted. Preferably, importation of peptides by a peptide transport system is decreased or eliminated. Peptide transport proteins are known in the art and include proteins or gene products encoded by peptide transport operons as discussed below and known in the art.

An "operon" as used herein refers to a cluster of genes that are all controlled by the same promoter. A peptide transport operon includes at least one gene encoding a peptide transport protein. Peptide transport operons include the opp operon and the dciA operon and homologs thereof. In one embodiment herein, a peptide transport operon excludes the opp operon. In another embodiment herein, a peptide transport protein excludes proteins encoded by the opp operon.

The opp operon has been reported as encoding an oligopeptide permease that is required for the initiation of sporulation and the development of genetic competence (Rudner et al, 1991, Journal of Bacteriology, 173:1388–1398). The opp operon is a member of the family of ATP-binding cassette transporters involved in the import or export of oligopeptides from 3–5 amino acids. There are five gene products of the opp operon: oppA is the ligand-binding protein and is attached to the outside of the cell by a lipid anchor; oppB and oppC are the membrane proteins that form a complex through which the ligand is transported; oppD and oppF (Perego et al., 1991, Mol. Microbiol. 5:173–185) are the ATPases thought to provide energy for transport (LeDeaux, J. R., et al., 1997, FEMS Microbiology Letters 153: 63–69). The opp operon has also been referred to as SpoOK by Rudner et al., 1991, J. Bacteriol. 173:1388–1398.

Opp operons are also disclosed in Podbielski et al. 1996, Molecular Microbiology 21: 1087–1099 and Tynkkynen et al. 1993, Journal of Bacteriology 175: 7523–7532. One assay for the presence or absence of a functioning opp operon is to subject the host to growth in the presence of toxic oligopeptide of 3 amino acids, such as Bialaphos, a tripeptide consisting of two L-alanine molecules and an L-glutamic acid analogue (Meiji Seika, Japan). A cell having a functional opp operon will have inhibited growth. A cell having a mutation in at least one gene of the opp operon gene cluster will not show growth inhibition in the presence of the toxic oligopeptide.

Further regarding peptide transport operons and peptides thereof, opp A,B,C,D, F of *Salmonella typhimurium* are further reported on in Hiles et al.,1987 J. Mol. Biol 195:125–142. OppA, B, C, D, F of *Bacillus subtilis* are further reported on in Perego, M., et al. Mol Microbiol 1991, 5, 173–185 and Rudner, D. Z., et al., J. Bacteriol 1991, 173(4):1388–1398. OppA, B, C, D, E of *E. coli* are reported on in Guyer, et al., 1985 J. Biol Chem 260:10812–10816. Also, a report has been made on amiA of *Streptococcus pneumonia* (Alloing, G 1994, J Mol Biol 241(1) :44–58. AppA, B, C, D, E of *B. subtilis* are reported on in Koide A. et al Mol Microbiol 1994 13(3) :417–426. Additionally, dppA of *E. coli* and *S. typhimurium* is reported on in Abouhamad et al 1991 Mol Microbiol 5(5):1035–1047. Furthermore, BldA, B, C, D, E of *Streptomyces coelicolor* are reported on in Nodwell, J. R. et al Mol Microbiol 1996, 22(5):881–93. OppA of Streptococcus is reported on in Podbielski, A et al Mol Microbiol 1996, 21(5):1087–1099. Moreover, TppA, B, C, D, E of *S. typhimurium* have been reported on in Gibson, M. M. et al., J. Bacteriol 1984 160:122–130. Moreover, it has been reported that oppA may also be obtained from *Chlamydia pneumonia*.

Organisms which a peptide transport operon or protein thereof can be obtained from include but are not limited to: *Aquifex aeolicus, Archaeoglobus fulgidus, Aeropyrum pernix, Bordetella pertussis, Bacillus subtilis, Clostridium acetobutylicum, Campylobacter jejuni, Chlorobium tepidum, Chlamydia pneumoniae* CWL029, *Chlamydia trachomatis* Serovar D, *Clostridium difficile, Corynebacterium diphtheriae, Deinococus radiodurans, Escherichia coli, Enterococcus faecalis, Haemophilus influenzae, Helicobacter pylori, Klebsiella pneumoniae, Mycobacterium leprae, Pseudomonas aeruginosa, Pyrococcus furiosus, Pyrococcus horikoshii, Pyrococcus abysii, Rhodobacter capsulatus, Streptococcus pyogenes* and *Salmonella typhimurium.*

The dciA operon has been reported on, see, e.g., Slack, et al., Mol Microbio (1991) 5(8), 1915–1925 and Mathlopoulos, et al., Mol Microbio (1991) 5(8), 1903–1913, as being a dipeptide transport operon in Bacillus. While this operon has been reported on, the function of each gene product has not previously been well characterized. Herein, provided are functions of the proteins of the dciA operon, including functional properties wherein a gene product is inactivated.

In one embodiment, dciAA is a peptide transport protein and inactivation of dciAA leads to increased polypeptide production and/or secretion. In another embodiment, inactivation of dciAE leads to decreased peptide transport and increased polypeptide production and/or secretion. In preferred embodiments, dciAA has RNA binding activity. Embodiments of dciAA, dciAB, dciAC, dciAD and dciAE are shown in FIGS. 2–6, respectively. DciA has homology to dpp of *E. coli*. Olson, et al., J Bacteriol 173:234–244 (1991); Kawarabayasi, Y., Journal DNA Res. 5 (2), 55–76 (1998).

In addition to those described above, homologs of peptide transport operons, peptide transport genes and peptide transport proteins can be identified by a number of methods. In one embodiment, a nucleic acid is a "peptide transport gene" if it encodes a protein having peptide transport activity as discussed above. Preferably, the overall homology of the nucleic acid sequence is preferably greater than about 60%, more preferably greater than about 75%, more preferably greater than about 80%, even more preferably greater than about 85% and most preferably greater than 90% of one of the dciA genes shown in FIG. 1, namely dciAA, dciAB, dciAC, dciAD or dciAE. In some embodiments the homology will be as high as about 93 to 95 or 98%.

In one embodiment, a protein is a "peptide transport protein" if it has peptide transport activity. Preferably the protein has overall homology greater than about 40%, more preferably greater than about 60%, more preferably at least 75%, more preferably greater than about 80%, even more preferably greater than about 85% and most preferably greater than 90% to the amino acid sequence of FIGS. 2, 3, 4, 5, or 6. In some embodiments the homology will be as high as about 93 to 95 or 98%.

Homology as used herein is in reference to sequence similarity or identity, with identity being preferred. This homology will be determined using standard techniques known in the art, including, but not limited to, the local homology algorithm of Smith & Waterman, Adv. Appl. Math. 2:482 (1981), by the homology alignment algorithm of Needleman & Wunsch, J. Mol. Biool. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387–395 (1984), preferably using the default settings, or by inspection.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403–410, (1990) and Karlin et al., PNAS USA 90:5873–5787 (1993). A particularly useful BLAST program is the WU-BLAST-2 program which was obtained from Altschul et al., Methods in Enzymology, 266: 460480 (1996). WU-BLAST-2 uses several search parameters, most of which are set to the default values. The adjustable parameters are set with the following values: overlap span= 1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical with the nucleotide residues of the sequence shown in the nucleic acid figures. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer nucleosides than those of the nucleic acid figures, it is understood that the percentage of homology will be determined based on the number of homologous nucleosides in relation to the total number of nucleosides. Thus, for example, homology of sequences shorter than those of the sequences identified herein and as discussed below, will be determined using the number of nucleosides in the shorter sequence.

In one embodiment, the peptide transport gene or operon is determined through hybridization studies. Thus, for example, nucleic acids which hybridize under high stringency to the nucleic acid sequences (that of the operon, the individual genes thereof or fragments thereof) identified in the figures, or a complement, are considered a peptide transport gene in one embodiment herein. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10 C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

Naturally occuring allelic variants of the genes and proteins provided herein may also be used in the methods of the present invention.

In addition to using the above techniques to find homologs of peptide transport genes, operons, proteins or peptide transport operon genes and proteins, one may use standard amplification of fragments of sequences as provided herein carried out in polymerase chain reaction (PCR) technologies such as described in Dieffenbach CW and GS Dveksler (1995, *PCR Primer, a Laboratory Manual,* Cold Spring Harbor Press, Plainview N.Y.). A nucleic acid sequence of at least about 10 nucleotides and as many as about 60 nucleotides from an operon gene as provided herein, preferably about 12 to 30 nucleotides, and more preferably about 20–25 nucleotides can be used as a probe or PCR primer.

The term "nucleic acid" as used herein refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed base and/or deoxyinosine residues (Batzer et al., *Nucleic Acid Res.* 19:5081 (1991); Ohtsuka et al., *J. Biol. Chem.* 260:2605–2608 (1985); Cassol et al., 1992; Rossolini et al., *Mol. Cell. Probes* 8:91–98 (1994)). The term nucleic acid is used interchangeably with gene, cDNA, and mRNA encoded by a gene.

"Protein" as used herein includes proteins, polypeptides, and peptides. As will be appreciated by those in the art, the nucleic acid sequences of the invention can be used to generate protein sequences. Preferred peptide transport proteins have peptide transport activity prior to inactivation and/or are controlled by a peptide transport operon.

The methods provided herein are applicable for production or secretion of polypeptides in a variety of cell types including eukaryote and prokaryote. For example, the cell can be selected from the group consisting of a plant cell, a mammalian cell, an insect cell, fungal cell, a gram-negative microorganism and a gram-positive microorganism.

Fungal cell or fungi as used herein include Chytridiomycetes, Hyphochrytridiomycetes, Plasmodiophoromycetes, Oomycetes, Zygomycetes, Trichomycetes, Ascomycetes, and Basidiomycetes. In one embodiment, filamentous fungi are used. Various species of filamentous fungi may be used as expression hosts including from the following genera: Aspergillus, Trichoderma, Neurospora, Penicillium, Cephalosporium, Achlya, Phanerochaete, Podospora, Endothia, Mucor, Fusarium, Humicola, Cochliobolus and Pyricularia. One embodiment includes *Penicillium chrysogenum*. One embodiment includes *Fusarium solani*. Specific expression hosts include *A. nidulans,* (Yelton, M., et al. (1984) Proc. Natl. Acad. Sci. USA, 81, 1470–1474; Mullaney, E. J. et al. (1985) Mol. Gen. Genet. 199, 37–45; John, M. A. and J. F. Peberdy (1984) Enzyme Microb. Technol. 6, 386–389; Tilburn, et al. (1982) Gene 26, 205–221; Ballance, D. J. et al. (1983) Biochem. Biophys. Res. Comm. 112, 284–289; Johnston, I. L. et al. (1985) EMBO J. 4, 1307–1311) *A. niger,* (Kelly, J. M. and M. Hynes (1985) EMBO 4, 475–479) *A. awamori,* e.g., NRRL 3112, ATCC 22342, ATCC 44733, ATCC 14331 and strain UVK 143f, *A. oryzae,* e.g., ATCC 11490, *N. crassa* (Case, M. E. et al. (1979) Proc. Natl. Acad. Scie. USA 76, 5259–5263; Lambowitz U.S. Pat. No. 4,486,553; Kinsey, J. A. and J. A. Rambosek (1984) *Molecular and Cellular Biology* 4, 117–122; Bull, J. H. and J. C. Wooton (1984) Nature 310, 701–704), *Trichoderma reesei,* e.g. NRRL 15709, ATCC 13631, 56764, 56765, 56466, 56767, and *Trichoderma viride,* e.g., ATCC 32098 and 32086.

In another embodiment, yeast cells are utilized or provided herein for production or secretion of polypeptides. Yeasts are suitable herein and include, but are not limited to, yeast capable of growth on methanol selected from the genera consisting of Hansenula, Candida, Kloeckera, Pichia, Saccharomyces, Torulopsis, and Rhodotorula. A list of specific species that are exemplary of this class of yeasts may be found in C. Anthony, *The Biochemistry of Methylotrophs,* 269 (1982). For example, Candida species includes but is not limited to *Candida albicans, Candida tropicalis, Candida* (*Torulopsis*) *glabrata, Candida parapsilosis, Candida lusitaneae, Candida rugosa* and *Candida pseudotropicalis.*

In one embodiment, the cell utilized or provided herein is a gram-negative microorganism. In one embodiment, the cell is from Enterobacteriaceae such as Escherichia, e.g., *E. coli,* Enterobacter, Erwinia, Klebsiella, Proteus, Salmonella, e.g., *Salmonella typhimurium,* Serratia, e.g., *Serratia marcescans,* Shigella or Pseudomonas such as *P. aeruginosa.*

In another embodiment, said cell is a gram-positive microorganism, preferably a member of the family Bacillus, although other gram-positive cells can be used such as those from Streptomyces. In a preferred embodiment, said cell is a gram-positive microorganism and is a member of the family Bacillus wherein said member of the family Bacillus is selected from the group consisting of *B. licheniformis, B. lentus, B. brevis, B. stearothermophilus, B. alkalophilus, B. amyloliquefaciens, B. coagulans, B. circulans, B. lautus, B. thuringiensis, B. methanolicus* and *B. anthracis.*

The polypeptide which is secreted or produced by the methods provided herein can be any polypeptide of interest. In a preferred embodiment, it is a heterologous polypeptide. Alternatively, the protein is homologous as discussed below.

In one aspect, the polypeptide to be produced and/or secreted is selected from the group consisting of hormone, enzyme, growth factor and cytokine. In one embodiment, the polypeptide is an enzyme. An enzyme as used herein includes but is not limited to (i) oxidoreductases; (ii) transferases, comprising transferase transferring one-carbon groups (e.g., methyltransferases, hydroxymethyl-, formyl-, and related transferases, carboxyl- and carbamoyltransferases, amidinotransferases) transferases transferring aldehydic or ketonic residues, acyltransferases (e.g., acyltransferases, aminoacyltransferas), glycosyltransferases (e.g., hexosyltransferases, pentosyltransferases), transferases transferring alkyl or related groups, transferases transferring nitrogenous groups (e.g., aminotransferases, oximinotransferases), transferases transferring phosphorus-containing groups (e.g., phosphotransferases, pyrophosphotransferases, nucleotidyltransferases), transferases transferring sulfur-containing groups (e.g., sulfurtransferases, sulfotransferases, CoA-transferases), (iii) Hydrolases comprising hydrolases acting on ester bonds (e.g., carboxylic ester hydrolases, thioester hydrolases, phosphoric monoester hydrolases, phosphoric diester hydrolases, triphosphoric monoester hydrolases, sulfuric ester hydrolases), hydrolases acting on glycosyl compounds (e.g., glycoside hydrolases, hydrolyzing N-glycosyl compounds, hydrolyzing S-glycosyl compound), hydrolases acting on ether bonds (e.g., thioether hydrolases), hydrolases acting on peptide bonds (e.g., aminoacyl-peptide hydrolases, peptidyl-amino acid hydrolases, dipeptide hydrolases, peptidyl-peptide hydrolases), hydrolases acting on C—N bonds other than peptide bonds, hydrolases acting on acid-anhydride bonds, hydrolases acting on C—C bonds, hydrolases acting on halide bonds, hydrolases acting on P—N bonds, (iv) lyases comprising carbon-carbon lyases (e.g., carboxy-lyases, aldehyde-lyases, ketoacid-lyases), carbon-oxygen lyases (e.g., hydro-lyases, other carbon-oxygen lyases), carbon-nitrogen lyases (e.g., ammonia-lyases, amidine-lyases), carbon-sulfur lyases, carbon-halide lyases, other lyases, (v) isomerases comprising racemases and epimerases, cis-trans isomerases, intramolecular oxidoreductases, intramolecular transferases, intramolecular lyases, other isomerases, (vi) ligases or synthetases comprising ligases or synthetases forming C—O bonds, forming C—S bonds, forming C—N bonds, forming C—C bonds.

The polypeptide of interest may be a therapeutically significant protein, such as growth factors, cytokines, ligands, receptors and inhibitors, as well as vaccines and antibodies.

In a preferred embodiment, the precursor mRNA for the polypeptide to be produced or secreted includes a putative RNase cleavage site or a binding site for a peptide transport protein. In preferred embodiments, the polypeptide to be produced or secreted includes a specific peptide transport protein recognition site. Preferably the recognition site is a binding site. Preferably, the recognition site is a binding site for dciAA.

As used herein, the term "heterologous protein" refers to a protein or polypeptide that does not naturally occur in the host cell. The term "homologous protein" or "endogenously expressed" refers to a protein or polypeptide native or naturally occurring in the host cell. In one embodiment, the invention includes host cells producing the homologous protein via recombinant DNA technology. A recombinant protein refers to any protein encoded by a nucleic acid which has been introduced into the host.

"Inactive protein" or grammatical equivalents as used herein refers to a reduction in the detectable activity of the protein when expressed in its wildtype form such as in its native unaltered host. Activities of peptide transport proteins include transport of dipeptides or oligopeptides of 3–7 amino acids, more preferably 5 or 6 amino acids, preferably in association with importation into the cell. In a preferred embodiment, peptide transport activity is reduced or eliminated.

In one aspect of the invention a gene product of a peptide transport operon is inactive or inactivated when the operon is activated. Preferably, the inactivated gene product is encoded by dciAA and/or dciAE. In a preferred embodiment, wildtype gene product corresponding to the inactive gene product comprises at least RNA binding or Rnase activity wherein the inactive gene product has decreased or eliminated interaction with RNA.

A peptide transport protein or a gene product of a peptide transport operon can be inactivated at the protein or nucleic acid level. It is understood that the cells and methods of the present invention may include more than one inactive protein. In one embodiment, two operons are utilized, an opp operon and a dciA operon. In one embodiment, at least one gene product from an opp operon and at least one gene product from a dciA operon is inactive.

While a number of examples are discussed herein, it is understood that inactivation can occur by one or more mutations or modifications in a gene, protein or operon, or a combination thereof. For example, in one embodiment, a mutation is made in the oppA operon and one mutation is made in the dciA operon, and more particularly in oppAA and dciAA. In another embodiment, 2 or more mutations are made to the same gene, protein or operon. In another embodiment, 2 or more mutations are made wherein the mutations occur in different genes of the same operon, or in different operons, wherein the mutations can be in the same gene or different genes when the mutations are made in different operons. Generally, as used is herein, mutation is used interchangeably with modification to refer to a change which infers inactivation of the gene, protein, system or activity as described herein.

In one aspect, the protein is inactivated because the gene encoding said protein has been mutated. The mutation can be caused in a variety of ways including one or more frameshifts, substitutions, insertions and/or deletions as further described below. The deletion can be of a single nucleotide or more, including deletion of the entire gene. It is understood that the cells comprising the inactive proteins described herein and methods of making said cells are also provided herein.

In one embodiment, a cell having an inactive protein as described herein is arrived at by the replacement and/or inactivation of the naturally occurring gene from the genome of the host cell. In a preferred embodiment, the mutation is a non-reverting mutation.

One method for mutating nucleic acid encoding a gene is to clone the nucleic acid or part thereof, modify the nucleic acid by site directed mutagenesis and reintroduce the mutated nucleic acid into the cell on a plasmid. By homologous recombination, the mutated gene may be introduced into the chromosome. In the parent host cell, the result is that the naturally occurring nucleic acid and the mutated nucleic acid are located in tandem on the chromosome. After a second recombination, the modified sequence is left in the chromosome having thereby effectively introduced the mutation into the chromosomal gene for progeny of the parent host cell.

Another method for inactivating the gene product is through deleting the chromosomal gene copy. In a preferred embodiment, the entire gene is deleted, the deletion occurring in such as way as to make reversion impossible. In another preferred embodiment, a partial deletion is produced, provided that the nucleic acid sequence left in the chromosome is too short for homologous recombination with a plasmid encoded gene.

Deletion of the naturally occurring gene can be carried out as follows. A gene including its 5' and 3' regions is isolated and inserted into a cloning vector. The coding region of the gene is deleted form the vector in vitro, leaving behind a sufficient amount of the 5' and 3' flanking sequences to provide for homologous recombination with the naturally occurring gene in the parent host cell. The vector is then transformed into the host cell. The vector integrates into the chromosome via homologous recombination in the flanking regions. This method leads to a strain in which the gene has been deleted.

The vector used in an integration method is preferably a plasmid. A selectable marker may be included to allow for ease of identification of desired recombinant microorganisms. Additionally, as will be appreciated by one of skill in the art, the vector is preferably one which can be selectively integrated into the chromosome. This can be achieved by introducing an inducible origin of replication, for example, a temperature sensitive origin into the plasmid. By growing the transformants at a temperature to which the origin of replication is sensitive, the replication function of the plasmid is inactivated, thereby providing a means for selection of chromosomal integrants. Integrants may be selected for growth at high temperatures in the presence of the selectable marker, such as an antibiotic. Integration mechanisms are described in WO 88/06623.

Integration by the Campbell-type mechanism can take place in the 5' flanking region of the gene, resulting in a strain carrying the entire plasmid vector in the chromosome in the locus. Since illegitimate recombination will give different results it will be necessary to determine whether the complete gene has been deleted, such as through nucleic acid sequencing or restriction maps.

Another method of inactivating the naturally occurring gene is to mutagenize the chromosomal gene copy by transforming a cell with oligonucleotides which are mutagenic. Alternatively, the chromosomal protease gene can be replaced with a mutant gene by homologous recombination.

In a preferred embodiment, the present invention encompasses host cells having further protease deletions or mutations. For example, well know protease deletions in Bacillus, including deletions or mutations in apr, npr, epr, mpr generally used for efficient heterologous expression. Other embodiments of the protease are described in, for example, U.S. Pat. No. 5,264,366.

Other ways of inactivating a protein at the nucleic acid level include the use of antisense molecules. Antisense or sense oligonucleotides, according to the present invention, comprise a fragment of the coding region of a peptide transport protein or a product of a peptide transport operon. Such a fragment generally comprises at least about 14 nucleotides, preferably from about 14 to nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988). Binding of antisense or sense oligonucleotides to target nucleic acid sequences results in the formation of duplexes that block transcription or translation of the target sequence by one of several means, including enhanced degradation of the duplexes, premature termination of transcription or translation, or by other means.

Ribozymes may also be used for inactivation in one embodiment. Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469–471 (1994), and PCT publication No. WO 97/33551 (published Sep. 18, 1997).

The peptide transport protein or product of a peptide transport operon may also be inactive or inactivated at the protein level. For example, the nucleic acid encoding the protein or gene product may be intact, but the cell may comprise an antagonist or inhibitor such as an antibody to inhibit the protein or gene product from having its native activity, such as peptide transport or RNA interaction activity. Moreover, the protein may be expressed as an inactive variant or be conditionally inactive, for example, by having temperature sensitive peptide transport.

For production and/or secretion of proteins in a cell, an expression vector comprising at least one copy of a nucleic acid encoding the heterologous or homologous protein, and preferably comprising multiple copies, is transformed into the cell under conditions suitable for expression of the protein.

Expression vectors used in the present invention comprise at least one promoter associated with the protein, which promoter is functional in the host cell. In one embodiment of the present invention, the promoter is the wild-type promoter for the selected protein and in another embodiment of the present invention, the promoter is heterologous to the protein, but still functional in the host cell. In one preferred embodiment of the present invention, nucleic acid encoding the polypeptide of interest is stably integrated into the host genome. Signal sequences may be added if needed.

In a preferred embodiment, the expression vector contains a multiple cloning site cassette which preferably comprises at least one restriction endonuclease site unique to the vector, to facilitate ease of nucleic acid manipulation. In a preferred embodiment, the vector also comprises one or more selectable markers. As used herein, the term selectable marker refers to a gene capable of expression in the host which allows for ease of selection of those hosts containing the vector. Examples of such selectable markers include but are not limited to antibiotics, such as, erythromycin, actinomycin, chloramphenicol and tetracycline.

In one embodiment of the present invention, nucleic acid encoding at least one polypeptide of interest is introduced into a host cell via an expression vector capable of replicating within the host cell. Suitable replicating plasmids for Bacillus are described in Molecular Biological Methods for Bacillus, Ed. Harwood and Cutting, John Wiley & Sons, 1990, hereby expressly incorporated by reference; see chapter 3 on plasmids. Suitable replicating plasmids for *B. subtilis* are listed on page 92. Several strategies have been described in the literature for the direct cloning of DNA in Bacillus. Plasmid marker rescue transformation involves the uptake of a donor plasmid by competent cells carrying a partially homologous resident plasmid (Contente et al., *Plasmid* 2:555–571 (1979); Haima et al., *Mol. Gen. Genet.* 223:185–191 (1990); Weinrauch et al., *J. Bacteriol.* 154(3): 1077–1087 (1983); and Weinrauch et al., *J. Bacteriol.* 169 (3):1205–1211 (1987)). The incoming donor plasmid recombines with the homologous region of the resident "helper" plasmid in a process that mimics chromosomal transformation.

Transformation by protoplast transformation is described for *B. subtilis* in Chang and Cohen, (1979) Mol. Gen. Genet 168:111–115; for *B.megaterium* in Vorobjeva et al., (1980) FEMS Microbiol. Letters 7:261–263; for *B. amyloliquefaciens* in Smith et al., (1986) Appl. and Env. Microbiol. 51:634; for *B.thuringiensis* in Fisher et al., (1981) Arch. Microbiol. 139:213–217; for *B.sphaericus* in McDonald (1984) J. Gen. Microbiol. 130:203; and B.larvae in Bakhiet et al., (1985) 49:577. Mann et al., (1986, Current Microbiol. 13:131–135) report on transformation of Bacillus protoplasts and Holubova, (1985) Folia Microbiol. 30:97) disclose methods for introducing DNA into protoplasts using DNA containing liposomes. The presence/absence of a marker gene can suggest whether the gene of interest is present in the host cell.

Alternatively, host cells which contain the coding sequence for the polypeptide of interest may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

There are various assays known to those of skill in the art for detecting and measuring activity of secreted polypeptides. In particular, for proteases, there are assays based upon the release of acid-soluble peptides from casein or hemoglobin measured as absorbance at 280 nm or calorimetrically using the Folin method (Bergmeyer, et al., 1984, Methods of Enzymatic Analysis vol. 5, Peptidases, Proteinases and their Inhibitors, Verlag Chemie, Weinheim). Other assays involve the solubilization of chromogenic substrates (Ward, 1983, Proteinases, in Microbial Enzymes and Biotechnology (W. M. Fogarty, ed.), Applied Science, London, pp. 251–317).

Means for determining the levels of secretion of a heterologous or homologous protein in a host cell and detecting secreted proteins include, using either polyclonal or monoclonal antibodies specific for the protein. Examples include enzyme-linked immunosorbent assay (ELISA), radioimmunoassay (RIA) and fluorescent activated cell sorting (FACS). These and other assays are described, among other places, in Hampton R et al (1990, *Serological Methods, a Laboratory Manual*, APS Press, St Paul Minn.) and Maddox D E et al (1983, J Exp Med 158:1211). In a preferred embodiment, secretion is higher using the methods and compositions provided herein than when using the same methods or compositions, but where a peptide transport protein or gene product of a peptide transport operon has not been inactivated. In a preferred embodiment, wherein RNase activity is decreased, production and/or secretion of polypeptides is increased. In another preferred embodiment, wherein peptide transport activity is decreased, production and/or secretion is increased.

A wide variety of labels and conjugation techniques are known by those skilled in the art and can be used in various nucleic and amino acid assays. Means for producing labeled hybridization or PCR probes for detecting specific polynucleotide sequences include oligolabeling, nick translation, end-labeling or PCR amplification using a labeled nucleotide. Alternatively, the nucleotide sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 and incorporated herein by reference.

The cells transformed with polynucleotide sequences encoding heterologous or homologous protein or endogenously having said protein may be cultured under conditions suitable for the expression and recovery of the encoded protein from cell culture. Other recombinant constructions may join the heterologous or homologous polynucleotide sequences to nucleotide sequence encoding a polypeptide domain which will facilitate purification of soluble proteins (Kroll D J et al (1993) DNA Cell Biol 12:441–53).

Such purification facilitating domains include, but are not limited to, metal chelating peptides such as histidine-tryptophan modules that allow purification on immobilized metals (Porath J (1992) Protein Expr Purif 3:263–281), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego CA) between the purification domain and the heterologous protein can be used to facilitate purification.

The manner and method of carrying out the present invention may be more fully understood by those of skill in the art by reference to the following examples, which examples are not intended in any manner to limit the scope of the present invention or of the claims directed thereto. All references cited herein are expressly incorporated herein in their entirety.

EXAMPLE 1

Example 1 illustrates the increase in production of subtilisin and amylase from *B. subtilis* having a mutation in the dciAE gene of the dciA operon.

Production of Subtilisin from Strains Containing a dciAE Wild Type or a dciAE Mutant in Shake Flasks Strains to be tested were grown in shake flasks containing 25 ml of LB (Difco) in a 250 mL flask. Shake flasks were incubated at 37° C. with vigorous shaking and at OD 550 of 0.8, 1 mL of culture were mixed with 0.5 ml 30% Glycerol and frozen for further experiments. 30 ul of the thawed vials were used to inoculate 40 ml of a media containing 68 g/L Soytone, 300 M PIPES, 20 g/L Glucose (final pH 6.8) in 250 mL flasks. The shake flasks are incubated at 37° C. with vigorous shaking for three days, after which they are sampled for subtilisin analysis of the supernatant.

Supernatants from liquid cultures were harvested after different times during growth and assayed for subtilisin as previously described (Estell, D. V., Graycar, T. P., Wells, J. A. (1985) *J. Biol. Chem.* 260, 6518–6521) in a solution containing 0.3 mM N-succinyl-L-Ala-L-Ala-L-Pro-L-Phe-p-nitroanalide (Vega Biochemicals), 0.1 M Tris, pH 8.6, at 25° C. The assays measured the increase in absorbance at 410 nm/min due to hydrolysis and release of p-nitroanaline. Table 1 describes the yields of protease produced from the two strains tested.

After 24 hours the strain deleted for dciAE secreted 3.5 times more subtilisin than the control. After 48 hours the increase is 4.9 times (Table 1).

TABLE 1

| *B. subtilis* strains | Genotype | Subtilisin (rate) 48 h |
|---|---|---|
| 2790 | dciAE wt | 0.888 |
| 2790 | dciAE- | 4.38 |

Production of Amylase from Strains Containing an dciAE Wild Type or an dciAE Mutant in Shake Flasks Strains to be tested were grown in shake flasks containing 25 ml of LB (Difco) in a 250 mL flask. Shake flasks were incubated at 37° C. with vigorous shaking and at OD 550 of 0.8, 1 mL of culture were mixed with 0.5 ml 30% Glycerol and frozen for further experiments. 30 ul of the thawed vials were used to inoculate 40 ml of a media containing 68 g/L Soytone, 300 M PIPES, 20 g/L Glucose (final pH 6.8) in 250 mL flasks. The shake flasks are incubated at 37° C. with vigorous shaking for several days during which they are sampled for amylase analysis of the supernatant.

Whole broth samples were spun down at different times of growth and their supernatants were assayed as follows. Supernatant is mixed in a cuvete with 790.0 ul of substrate (Megazyme-Ceralpha-Alpha Amylase; substrate is diluted in water and is used as 1 part substrate plus 3 parts of Alpha Amylase buffer pH 6.6) at 250 C. Alpha Amylase buffer is composed of 50 mM Maleate Buffer, 5 mM CaCl2, and 0.002% Triton X-100, PH=6.7. Amylase was measured in a Spectronic Genesys 2 Spectophotometer using a protocol for amylase activity (Wavelength: 410 nm, Initial Delay: 75 secs., Total Run Time: 120 secs, Lower Limit: 0.08, Upper Limit: 0.12).

Results show that the strain containing the dciAE deletion produced 1.8 times more amylase at 48 hours than when the dciAE wild-type gene was present. At 60 hours the increase is 2.5 times (Table 2).

Table 2 describes the yields of amylase produced from the two strains tested.

TABLE 2

| B. subtilis strains | Genotype | Amylase (rate) 48 h | 60 h |
|---|---|---|---|
| 2790 | dciAE wt | 0.054 | 0.066 |
| 2790 | dciAE- | 0.098 | 0.168 |

EXAMPLE 2

Example 2 illustrates the additional increase of production of subtilisin from *B. subtilis* having a mutation in the oppAA of the oppA operon and a deletion of dciAA gene of the dciA operon.

Production of Recombinant Subtilisin from Strains Containing a dciAA Deletion and an oppAA Mutation in Shake Flasks Strains to be tested were grown in shake flasks containing 25 ml of LB (Difco) and 25 ug/L chloramphenicol in a 250 ml flasks. Shake flasks were incubated at 37° C. with vigorous shaking and at OD 550 of 0.8, 1 ml of culture were mixed with 0.5 ml 30% Glycerol and frozen for further experiments. 25 ml of FNA34EB media (Per liter: 90.72 g PIPES acid form, pH to 6.8, 34.00 g Soytone (Difco), 2 drops of Mazu DF-204, 40 mL 50% glucose) in 250 ml flasks.

10 uL of glycerol stocks from the strains to be tested was added to each flask. Once inoculated, the flasks were incubated at 37 degrees C., 250 rpm and samples were taken every 24 hours until 75 hours. 1-mL samples were taken out in the sterile hood and measured for OD 550. Samples were centrifuged for 1 minute to pellet cells.

Supernatants from liquid cultures were harvested after different times during growth and assayed for subtilisin as previously described (Estell, D. V., Graycar, T. P., Wells, J. A. (1985) *J. Biol. Chem.* 260, 6518–6521) in a solution containing 0.3 mM N-succinyl-L-Ala-L-Ala-L-Pro-L-Phe-p-nitroanalide (Vega Biochemicals), 0.1 M Tris, pH 8.6, at 25° C. The assays measured the increase in absorbance at 410 nm/min due to hydrolysis and release of p-nitroanaline.

Table 3 describes the yields of protease produced from the two strains. Results show that the strain containing the dciAA deletion and the oppAA mutation produced 1.9 more protease than when the dciAA wild-type was present.

TABLE 3

| | | Subtilisin (mg/L) | | |
|---|---|---|---|---|
| B. subtilis strains | Genotype | 27 h | 51 h | 75 h |
| 001 | oppAA- | 30 | 105 | 138 |
| 040 | oppAA- dciAA- | 28 | 124 | 262 |

The effect found deleting the dciAA protein in increase enzyme production could be due to the possible interaction between this protein and the subtilisin (apr) mRNA. As demonstrated in the next section we show there is some homology between dciAA and proteins that interact with the RNA, furthermore, we show that we found fact that there is a "putative Rnase cleavage site" in the untranslated mRNA region of subtilisin (starting in the +1 mRNA). This putative RnaseE cleavage site in subtilisin has 6/7 identity with a site identified in RNA I (table 4). This site is cleavaged by RNAase E (Tomcsanyi and Cohen S 1985; Lin-Chao and Cohen S 1991; Lin-Chao et al 1994). The putative Rnase E site has 7/7 identity with the demonstrated cleavage site for RnaseE in 9S RNA (Roy, M. K., and Apirion, D., Biochim. Biophys. Acta 747, 200–208 1983) (Table 4).

TABLE 4

| RNA | location | Sequence |
|---|---|---|
| Subtilisin | +1 5' mRNA | ACAGAAU (SEQ ID NO: 7) |
| RNA I | +1 5' mRNA | ACAGUAU (SEQ ID NO: 8) |
| 9S RNA | +1 5' mRNA | ACAGAAU (SEQ ID NO: 9) |

Without being bound to theory, we believe that it could be possible that one of the functions of the dciAA protein is binding to this region of the RNA affecting the stability of this RNA or the translation of the protein. Thus, also provided herein is a method of increasing peptide production/secretion of proteins that contain a putative dciAA recognition site.

Homology Between dciAA and Other Proteins

The predicted product of the dciAA gene was used to search a translation of the GeneBank data base and blast homology was found between the dciAA gene product and the dppA protein from *B. methanolicus* (75% identity), a putative peptide ABC transporter from *Deinocuccus radiodurans* (33% identity), and with the dppA dipeptide transport protein from *Pyrococcus abyssi* (28%). The search program used was BSORF by fasta 3 t and blast. Several dipeptide proteins from *B. methanolicus* 75% shows identity with a putative transport associated protein in *Streptomyces coelicolor*, 32% identity with a dipeptide transport protein dppA from *Pyrococcus abyssi*.

By doing the search using different regions of the dciAA protein in the GeneBank database (BSORF by fasta 3 t and blast) homology was found between the dciAA gene product with a ribonuclease from *E. coli* (Rnase E aka Ams) (Claverie-Martin et al J. Biol. Chem. 266: 2843–2851, 1991). Both proteins shows a 25% identity (and 48% conservative substitutions) over a region of 47 amino acids in the carboxy-terminal portions of both proteins. DciAA also share 26% identity with the carboxy-terminal portion of ribonucleoprotein La from Homo sapiens (Chan et al Nucleic Acid Research 17, 2233–2244,1989).

Homology Between dciAE and Other Proteins

The predicted product of the dciAE was used to search a translation of the GeneBank data base. The search program used was BSORF by festa 3t and blast. Homology was formed within OPPA oligopeptide-binding protein OppA of *B. subtilis* (40% identity) pX02-66 of *B. anthracis* (32% identity), Trac of *Enterococcus faecalis* (30% identity), MppA periplasmic murein peptide-binding protein precursor of *E. coli* (30% identity), OppA-Salty periplasmic oligopeptide-binding protein (oligopeptide-binding protein precursor) of *Salmonella typhimurium* (30% identity), oligopeptide permease homolog All (*Borrelia burgdorferi*) (29% identity), oligopeptide ABC transporter, periplasmic oligopeptide-binding protein (OppAV) homolog-lyme disease spirochete *Borrelia burgdorferi*), oligopeptide-binding protein from *Chlamydophila pneumonia* (26% identity), and to some extent, oligopeptide ABC transporter periplasmic binding protein OppA-syphilis spirochaete from *Treponema pallidum* (26% identity).

Deletion of the Dipeptide Transport System dciAA Gene

Using the PCR technique, 647 bp of the dciAA gene present in strains 001 and BG2790 was deleted. Two amplified DNA fragments containing part of the 5' (using primers dci1.f and dci3.3) and 3' of the gene (using primers dci2.r and dci4.0 were ligated and cloned in a pTSpUC19Kan plasmid. Plasmid pTSpUC19Kan carries a Kanamycin resistance gene (Kanr) and a temperature sensitive origin of replication (TsOri). The dciAA disruption plasmid, pMdci, was protoplast transformed into the two strains. Because of the TsOri, this plasmid integrated into the chromosome at the region of homology with the dciAA gene when cultured under selective pressure at the non-permissive temperature, e.g. 48° C. After integration, strains carrying the integrated plasmid were grown extensively at permissive temperature. Upon excision of the integrated plasmid, either the parent strain 001 or BG2790 is restored, or strains carrying the deleted gene is constructed. Two new strains were confirmed by PCR amplification of the gene with primers based in the gene sequence to contain the deletion of the gene.

Deletion of the Dipeptide Transport System dciAE Gene

Using the PCR technique, 1228 bp of the dciAE gene present in strain BG2970 was deleted. Two amplified DNA fragments containing part of the 5' (using primers dciAE1 and dciAE2) and 3' of the gene (using primers dciAE3 and dciAE4) were ligated and cloned in a pTSpUC19Kan plasmid. Plasmid pTSpUC19Kan carries a Kanamycin resistance gene (Kanr) and a temperature sensitive origin of replication (TsOri). The dciAE disruption plasmid, pMdciE, was protoplast transformed into the BG2790 production strain. Because of the TsOri, this plasmid integrated into the chromosome at the region of homology with the dciAE gene when cultured under selective pressure at the non-permissive temperature, e.g. 48° C. After integration, three strains carrying the integrated plasmid were grown extensively at permissive temperature. Upon excision of the integrated plasmid, either the parent strain BG2790 is restored, or a strain carrying the deleted gene is constructed. The new strain was confirmed by PCR amplification of the gene with primers based in the gene sequence to contain the deletion of the gene.

Primers:
dci1.f
GCGCGCGGATCCCGTCTGAATGAATTGTTATCGGTT TTCAGCCGTGTACGGG (SEQ ID NO: 10)
dci2.r
GCGCGCCTGCAGCGGGATGGAGATGCCGAGTAC TGCAAGACTCATCGCGGCG (SEQ ID NO: 11)
dci3.r
GCGCGCGTCGACCCATATCTACTGACATGTACAATT TCATAACGC (SEQ ID NO: 12)
dci4.f
GCGCGCGTCGACGCCGCTCACACCGCCTGACAGG CCAGTTCTGAGC (SEQ ID NO: 13)
dciAE1
GCGCGCGGATCCGATGTGTCTGTCATTCTGATT ACGC (SEQ ID NO: 14)
dciAE2
GCGCGCGTCGACGATCGGCGGATCGAATGMGTC GG (SEQ ID NO: 15)
dciAE3
GCGCGCGTCGACCCAATAAAGAATACGATCAGCTG ATC (SEQ ID NO: 16)
dciAE4
GCGCGCCTGCAGTGTCCCAAAACCCCCGATGC GCAC (SEQ ID NO: 17)

EXAMPLE 3

Example 3 illustrates a method for screening for microorganisms with 40 increased production of proteins, preferably secreted proteins. More particularly, the method is for screening for cells having interrupted peptide transport activity, particularly an inhibition in import of peptides, which results in an increase in production of polypeptides. The method involves subjecting cells to a toxic peptide which is the size of a peptide which would normally be imported into the cell by the peptide transport system. In a preferred embodiment, the toxic peptide is Bialaphos. Bialaphos is a tripeptide consisting of two L-alanine molecules and an L-glutamic acid analogue. When digested by peptidases it is deleterious to the cell. It is an antibiotic, see, Meiji Seika, Japan.

There has been reported in the literature that at least one operon in Bacillus is involved in the uptake of molecules of the size of Bialaphos (3-amino acids), the oppA operon. There may also be other additional genes involved in Bialaphos uptake.

The method allows an efficient method for screening for cells which have interrupted peptide transport and increased production of polypeptides. Specifically, the method screens for mutation(s) which result in decreased peptide uptake. Cells which survive exposure to Bialaphos are identified as having one or more such mutations. The method does not require further characterization of the mutation, for example, at the nucleic acid level, thereby providing efficiency. However, further screening can occur such as for increased production of polypeptides, and further characterization and optimization of the mutation(s). Exposure to Bialaphos can occur in a number of ways such as plating cells with Bialaphos, for example, 50 ug/ml.

The interrupted peptide transport can occur because the strain is mutated, or because the cell has been mutated, or because genes, proteins or operons have been mutated or modified so as to result in increased polypeptide production as described herein. Any one or all of the genes in one or more peptide transport operons may be mutated or modified.

A microorganism or cell having a functional peptide transport operon, for example, the opp operon, will have inhibited growth. A microorganism having a mutation in at least one gene of the opp operon gene cluster will not show growth inhibition in the presence of the toxic oligopeptide Method to Obtain Bialaphos Resistant Mutants Cells are grown in liquid culture (LB) until they reach exponential phase. Cultures are plated onto Bacillus minimal Agar plates containing different concentrations of Bialaphos. Plates are incubated overnight at 37° C. and growing colonies are streaked out for purification on same type of plates. These new strains are Bialaphos resistance and all produce more protease than the parental strain after overnight growth.

Protease Assay

Supernatants from liquid culture were harvested after 3 days of growth and assayed for subtilisin as previously described (Estell, D. V., Graycar, T. P., Wells, J. A. (1985) *J. Biol Chem.* 260:6518–6521) in a solution containing 03 mM N-succinyl-L-Ala-L-Ala-L-Pro-L-Phe-p-nitroanalide (Vega Biochemicals), 0.1 M Tris, pH 8.6, at 25° C. The assays measured the increase in absorbance at 410 nm/min due to hydrolysis and release of p-nitroanaline. The results were easily detectable and confirmed that one can identify cells having increased protein production by screening for cells which do not uptake peptides.

What is claimed is:

1. A method of increasing secretion of a polypeptide in a cell wherein said cell is a member of the genus Bacillus that expresses at least one peptide transport protein comprising:

inactivating at least one peptide transport protein in said cell, wherein said peptide transport protein is encoded by an operon selected from the group consisting of the decoyinine inducible (dciA) operon, and the oligonucleotide ABC transporter (opp) operon; and culturing said cell under conditions suitable for expression and secretion of said polypeptide.

2. The method of claim 1 wherein said member of the genus Bacillus is selected from the group consisting of and B. licheniformls, B. lentus, B. brevus, B. stearothermophilus, B. alkalophilus, B. amylotiquefaciens, B. coagulans, B. circulans, B lautus, B. methoanolicus, B. anthracis and B. thuringiensis.

3. The method of claim 1 wherein said polypeptide is selected from the group consisting of hormones, enzymes, growth factors, and cytokines.

4. The method of claim 1 wherein said polypeptide is heterlogous.

5. The method of claim 1 wherein said polypeptide is an enzyme selected from the group consisting of proteases, carbohydrases, reductases, lipases, isomerases, transferases, kinases, phosphatases, cellulase, endoglucosidase H, oxidases, alpha-amylases, glucoamylases, lignocellulose, hemicellulase, pectinase, and ligninase.

6. The method of claim 1 wherein said polypeptide is a Bacillus amylas.

7. The method of claim 1 wherein said polypeptide is subtilisin.

8. The method of claim 1 wherein said polypeptide is amylase.

9. The method of claim 8 wherein said polypeptide is Bacillus amylase.

10. The method of claim 1 wherein said inactivating comprises mutating a nucleic acid encoding said peptide transport protein.

11. The method of claim 10 wherein said mutating causes a frameshift.

12. The method of claim 10 wherein said mutating is deleting one or more nucleotides.

13. A method of producing a polypeptide in a Bacillus cell comprising the steps of:

a) obtaining a cell comprising nucleic acid encoding a polypeptide to be produced, said cell further comprising a peptide transport operon wherein at least one gene product of said peptide transport operon is inactive in said cell, and further wherein said peptide transport operon is selected from the group consisting of the decoyinine inducible (dciA) operon, and the oligonucleotide ABC transporter (opp) operon; and b) culturing said cell under conditions suitable for expression such that said polypeptide is produced.

14. The method of claim 13 wherein said polypeptide is heterolgous.

15. The method of claim 13 wherein said gene product is inactive as the result of a mutation in said operon.

16. The method of claim 15 wherein said mutation is a frameshift mutation.

17. The method of claim 15 wherein said mutation is a deletion of one or more nucleotides.

* * * * *

UNITED STATES PATENT AND TRADEMARK OFFICE
CERTIFICATE OF CORRECTION

PATENT NO. : 6,544,792 B1
APPLICATION NO. : 09/595386
DATED : April 8, 2003
INVENTOR(S) : Maria R. Diaz-Torres It is certified that error appears in the above-identified patent and that said Letters Patent is hereby corrected as shown below:

In Column 37, Claim 2
On line 41, replace "B. *licheniformls*" with --*B. licheniformis*--.
On line 42, replace "B. *amylotiquefaciens*" with --*B. amyloliquefaciens*--.

In Column 37, Claim 4
On line 49, replace "heterlogous" with --heterologous--.

In Column 37, Claim 5
On line 54, replace "lignocellulose" with --lignocellulase--.

In Column 37, Claim 6
On line 57, replace "amylas" with --protease--.

In Column 38, Claim 8
On line 27, insert the word --an-- between "is" and "amylase".

In Column 38, Claim 9
On line 29, insert the word --a-- between "is" and "Bacillus".

In Column 38, Claim 14
On line 51, replace "heterlogous" with --heterologous--.

Signed and Sealed this

Twelfth Day of August, 2008

JON W. DUDAS
*Director of the United States Patent and Trademark Office*

SEQUENCE LISTING

<160> NUMBER OF SEQ ID NOS: 17

<210> SEQ ID NO 1
<211> LENGTH: 5798
<212> TYPE: DNA
<213> ORGANISM: Artificial Sequence
<220> FEATURE:
<223> OTHER INFORMATION: dciA operon coding sequence

<400> SEQUENCE: 1

```
ccggacgttt ttgatgaggt atttgaaaga accctgagaa aatatgaact gcttacagaa      60
caggttggta aacaaacatg aatccttgaa agaggattct tttttttatca ctgaatgatt     120 gagattttc ccagttatat tgcatttttc ctctttttt aatataattt gttagaatat        180
tcataattta gtaaaaaagg aggagcgtta tgaaattgta catgtcagta gatatggaag      240
gtatttcggg tcttccggac gataccttttg tggattccgg caagcggaat tatgaacgcg     300
gacggcttat catgactgaa gaagcaaact actgtattgc tgaagcgttt aacagcgggt      360
gtaccgaggt gctggtcaat gacagtcatt cgaagatgaa taatctgatg gttgaaaagc     420
ttcaccctga agcagacttg atttctggtg acgtcaaacc attttcaatg gtggagggac     480
tggatgatac gtttagaggc gctttgtttc tcggttatca tgcgagagcc tcgactcctg     540
gtgtcatgtc acacagcatg attttcggcg tccgtcattt ttacataaac gatcggcctg      600
tcggtgagct tggattaaat gcatacgttg ccggttatta tgatgtcccg gtattaatgg     660
tagccgggga tgaccgggcg gcgaaggaag cagaagagct tatcccgaac gtgacgacag     720
ccgcagtcaa acaaaccatt tcaagatccg cagtgaagtg cttgtcgcct gcgaaagccg     780
gacggctgtt gacagaaaaa acgccatttg ccctgcaaaa caaggacaaa gtcaagccgc     840
tcacaccgcc tgacaggcca gttctgagca ttgaattcgc caattatggc caagcagaat     900
gggcgaatct gatgccggga acgaaatca agacgggaac tacaaccgtt caatttcagg      960
cgaaggacat gcttgaagcc tatcaggcga tgcttgtcat gactgagctt gcgatgcgga    1020
catcattctg ctaaaggggt gttttaggct ttggcgcgat acatgataaa gcgttttttgg    1080 gcaatggcag ctacgatttt ggtgattacc accctgactt ttgttctcat gaaggtcatt    1140
cccggatctc cttttaacga ggagagaggc acaaatgaag ccgttcaaaa aaatctcgaa    1200
gcctactatc acttagacga tcctctcatt ttccaataca tttctactt aaaatccatc    1260 attacattcg atttcggacc ttcaattaaa aaaccgtcgg acagcgtaaa tgatatgctg    1320
gaacgcggat ttcccgtttc ctttgagctt gggatgacag cgattgtcat tgctgtgatt    1380
tctgggctgg tgctgggcgt aatcgctgca ctccgccgca atggcttttt ggactacgcc    1440
gcgatgagtc ttgcagtact cggcatctcc atcccgaatt ttattctggc aacattgctc    1500
attcagcaat ttgctgtcaa tctcaaacta tttcccgctg cgacatggac gagcccgatt    1560
catatggtgc ttccgaccgc agcgcttgct gtagggccaa tggcgatcat tgccaggctg    1620
```

-continued

```
acacggtcga gcatggtcga agttctgaca caggattata tccgcacagc aaaagcaaaa      1680
gggctttctc cgttcaaaat tatcgtaaaa cacgcactca gaaatgcact catgcccgtc      1740
attaccgtcc tgggcacact cgtcgccagc atcttaacag gaagctttgt cattgaaaaa      1800
atctttgcca ttccgggaat gggaaaatat tttgttgaaa gcattaatca gcgggactac      1860
cccgtgatta tgggaacgac cgttttttac agcgtcattc tgattatcat gctgttttg      1920
gtcgatttgg cctacggtct cttagacccg cgcattaaac tgcataagaa agggtgaagc      1980
gtgtgaatct ccctgtacaa acggatgaac gccagccaga acagcacaat caggtgcctg      2040
atgagtggtt tgtcttgaat caggaaaaaa atcgggaagc cgattcggtc aagcggccga      2100
gtttgtcata cacgcaggat gcctggagga ggctgaaaaa aaataaatta gcgatggccg      2160
gactctttat tcttttattt cttttttgtca tggcagttat cgggccctttt ttatcgcccc    2220
atagtgtcgt acgccaatcg ctgacagaac aaaatcttcc gccctcagcc gatcattggt      2280
tcggcaccga tgaactcggc cgggatgtgt ttacccgaac atggtatggc gcgagaatct      2340
cgttgtttgt cggcgtgatg gcagcactga ttgattttt gatcggtgtc atttacggag      2400
gcgttgccgg ctataaaggc ggcaggattg acagcattat gatgcggatt atcgaagtgc      2460
tgtacggact gccgtatctg cttgttgtca ttttgctgat ggtgctcatg ggaccgggac      2520
tgggcacgat tattgtggcg ctgactgtga ccgggtgggt cggcatggcg agaattgtaa      2580
gaggccaggt gcttcagatt aaaaattatg aatatgtact cgcctcgaaa acctttggcg      2640
cgaaaacctt tcgcatcatc cggaagaatt tgctgcgcaa tactatggga gcgatcatcg      2700
tacaaatgac attaaccgta cctgccgcca tattcgcaga atcattttta agctttctcg      2760
gcctgggcat acaggctccg tttgcaagtt ggggcgtgat ggcgaatgac ggcctgccta      2820
cgatttttatc tgggcattgg tggcgcctgt ttttccggc cttttcata tcttcgacga       2880
tgtacgcgtt taatgtgctg ggggacggat tgcaggatgc gcttgaccct aagctgagga      2940
ggtgactgta tggaaaaagt tctgtcagtc caaaatctgc acgtgtcttt tacgacttac      3000
ggcgggacgt tcaggcggt cagaggggtg agctttgatt tgtataaagg agaaaccttt        3060
gcgatcgtcg gcgaatccgg ctgcggcaaa agcgttacct cccaaagcat catgggcctg      3120
cttccgcctt attcggcgaa ggtgacagac ggcaggattc tatttaaaaa caagaccctt      3180
tgccgtctct ctgacaaaga aatgagaggt ataagggag ccgacatttc tatgattttt       3240
caagacccga tgacggcgtt aaaccctacg ctgactgtcg gcgaccagct gggggaagcg      3300
ctattgcgcc acaaaaaat gagcaaaaaa gcggcacgga agaggtgct ttccatgctg        3360
tcattggttg gtattccaga tcccggagag cgcctaaagc aatatcccca ccaattcagc      3420
ggcggtatga gacagcggat tgtcattgcg atggcgctga tttgcgagcc tgatatctta      3480
attgcggatg aaccgaccac cgccctggat gtaaccattc aggcacagat tttagagctg      3540
tttaaagaga ttcagagaaa acggatgtg tctgtcattc tgattacgca cgatttaggg       3600
gttgttgccc aggtagctga cagagtcgca gtcatgtatg ccgggaaaat ggcggaaatc      3660
ggcacaagaa aagatatttt ttatcagccg cagcacccat atacaaaagg cctgctgggc      3720
tctgtcccgc ggctggattt aaatggcgct gagctgaccc cgattgacgg aacgccgccg      3780
gatttatttt cgcctccgcc gggctgcccg tttgccgccc gctgtccgaa caggatggtt      3840
gtgtgtgaca gggtgtaccc gggccagacg atcagatctg actcgcacac cgtcaactgc      3900
tggctgcagg atcaacgagc agagcatgcg gtgctgtcag gagatgcgaa ggattgaaca      3960
tgaaaagggg gaagaggatg aaacgagtga aaaagctatg gggcatgggt cttgcattag      4020
```

```
gactttcgtt tgcgctgatg gggtgcacag caaatgaaca ggccggaaaa gaaggcagtc    4080
atgataaggc aaaaaccagc ggagaaaagg tgctgtatgt aaataatgaa atgaaccga     4140 cttcattcga tccgccgatc ggctttaata atgtgtcatg gcagccgtta aataacatca    4200 tggagggggct gacgcgtctt ggcaaagatc atgagcccga gccggcaatg gcggagaaat   4260
ggtctgtttc gaaagataat aaaacttaca catttacgat tcgggaaaat gcgaaatgga    4320
caaacggaga tcctgtaaca gccggagact tcgaatacgc gtggaagcgg atgcttgatc    4380
cgaaaaaagg cgcttcatcg gcattcctag gttattttat tgaaggcggc gaagcatata    4440
acagcgggaa agggaaaaaa gacgatgtga aggtgacggc aaaggatgat cgaacccttg    4500
aagttacact ggaagcaccg caaaatatt tcctgagcgt tgtgtccaat cccgcgtatt     4560
tcccggtaaa tgaaaaggtc gataaagaca atccaaagtg gtttgctgag tcggatacat    4620
ttgtcggaaa cggcccgttt aagctgacgg aatggaagca tgatgacagc atcacaatgg    4680
agaaaagcga cacgtattgg gataaggata cagtgaagct tgataaggtg aaatgggcga    4740
tggtcagtga cagaaataca gattaccaga tgtttcaatc aggggaactt gataccgctt    4800
atgtccctgc tgagctgagt gatcagctgc ttgatcagga taacgtcaat attgttgacc    4860
aggcgggtct ctatttctat cgatttaatg tcaacatgga gccgttccaa aatgaaaaca    4920
tcagaaaagc ctttgcgatg gctgtggatc aagaggaaat tgtaaagtac gtcacgaaaa    4980
ataatgaaaa accggcgcac gccttttgtat cgcctgggtt tacgcagcct gacggcaaag    5040
atttccgtga agcaggcgga gacctgatca agcctaacga aagcaaagcg aagcagctgc    5100
tcgaaaaggg catgaaggaa gaaaactata ataagcttcc tgcgatcacg cttacttaca    5160
gcacaaagcc ggagcataaa aagattgccg aagctattca gcaaaaattg aaaaatagcc    5220
ttggagtcga tgtgaagctg gccaatatgg aatggaacgt attttttagag gatcaaaaag   5280 cgctgaaatt ccaattctct caaagctcat ttttgcctga ttatgcagac cctatcagtt    5340
ttctggaagc ctttcaaacg ggaaattcga tgaaccgcac aggctgggcc aataaagaat    5400
acgatcagct gatcaaacag gcgaaaaacg aagccgatga aaaacacgg ttctctctta    5460 tgcatcaagc tgaagagctg ctcatcaatg aagcgccgat cattccggtt tatttttata    5520
atcaggttca cctgcaaaat gaacaagtaa aaggaattgt ccgtcaccct gtcggctata    5580
tcgatttaaa atgggcagat aaaaactgat ggaggcgatt gaggaaatac tgcttctta    5640 tgcgaaggag cggtatttt tctctttctt gcacgtatac gtagggtgca gagcaaatga    5700
aaggagtgtt ttcgttgaat tacaagccga aagcgttgaa caagggtgat acagtcggag    5760
tgatcgcgcc cgcaagtccg ccggatccaa aaaagctt                           5798
```

<210> SEQ ID NO 2
<211> LENGTH: 274
<212> TYPE: PRT
<213> ORGANISM: Artificial Sequence
<220> FEATURE:
<223> OTHER INFORMATION: amino acid sequence for dciAA

<400> SEQUENCE: 2

Met Lys Leu Tyr Met Ser Val Asp Met Glu Gly Ile Ser Gly Leu Pro
1               5                   10                  15

Asp Asp Thr Phe Val Asp Ser Gly Lys Arg Asn Tyr Glu Arg Gly Arg
            20                  25                  30

Leu Ile Met Thr Glu Glu Ala Asn Tyr Cys Ile Ala Glu Ala Phe Asn
        35                  40                  45

```
Ser Gly Cys Thr Glu Val Leu Val Asn Asp Ser His Ser Lys Met Asn
    50                  55                  60

Asn Leu Met Val Glu Lys Leu His Pro Glu Ala Asp Leu Ile Ser Gly
65                  70                  75                  80

Asp Val Lys Pro Phe Ser Met Val Glu Gly Leu Asp Asp Thr Phe Arg
                85                  90                  95

Gly Ala Leu Phe Leu Gly Tyr His Ala Arg Ala Ser Thr Pro Gly Val
                100                 105                 110

Met Ser His Ser Met Ile Phe Gly Val Arg His Phe Tyr Ile Asn Asp
            115                 120                 125

Arg Pro Val Gly Glu Leu Gly Leu Asn Ala Tyr Val Ala Gly Tyr Tyr
            130                 135                 140

Asp Val Pro Val Leu Met Val Ala Gly Asp Asp Arg Ala Ala Lys Glu
145                 150                 155                 160

Ala Glu Glu Leu Ile Pro Asn Val Thr Thr Ala Ala Val Lys Gln Thr
                165                 170                 175

Ile Ser Arg Ser Ala Val Lys Cys Leu Ser Pro Ala Lys Ala Gly Arg
                180                 185                 190

Leu Leu Thr Glu Lys Thr Pro Phe Ala Leu Gln Asn Lys Asp Lys Val
            195                 200                 205

Lys Pro Leu Thr Pro Pro Asp Arg Pro Val Leu Ser Ile Glu Phe Ala
        210                 215                 220

Asn Tyr Gly Gln Ala Glu Trp Ala Asn Leu Met Pro Gly Thr Glu Ile
225                 230                 235                 240

Lys Thr Gly Thr Thr Thr Val Gln Phe Gln Ala Lys Asp Met Leu Glu
                245                 250                 255

Ala Tyr Gln Ala Met Leu Val Met Thr Glu Leu Ala Met Arg Thr Ser
                260                 265                 270

Phe Cys

<210> SEQ ID NO 3
<211> LENGTH: 308
<212> TYPE: PRT
<213> ORGANISM: Artificial Sequence
<220> FEATURE:
<223> OTHER INFORMATION: amino acid sequence for dciAB

<400> SEQUENCE: 3

Met Ala Arg Tyr Met Ile Lys Arg Phe Trp Ala Met Ala Ala Thr Ile
1               5                   10                  15

Leu Val Ile Thr Thr Leu Thr Phe Val Leu Met Lys Val Ile Pro Gly
                20                  25                  30

Ser Pro Phe Asn Glu Glu Arg Gly Thr Asn Glu Ala Val Gln Lys Asn
            35                  40                  45

Leu Glu Ala Tyr Tyr His Leu Asp Asp Pro Leu Ile Phe Gln Tyr Ile
    50                  55                  60

Phe Tyr Leu Lys Ser Ile Ile Thr Phe Asp Phe Gly Pro Ser Ile Lys
65                  70                  75                  80

Lys Pro Ser Asp Ser Val Asn Asp Met Leu Glu Arg Gly Phe Pro Val
                85                  90                  95

Ser Phe Glu Leu Gly Met Thr Ala Ile Val Ile Ala Val Ile Ser Gly
                100                 105                 110

Leu Val Leu Gly Val Ile Ala Ala Leu Arg Arg Asn Gly Phe Leu Asp
            115                 120                 125
```

```
Tyr Ala Ala Met Ser Leu Ala Val Leu Gly Ile Ser Ile Pro Asn Phe
    130                 135                 140
Ile Leu Ala Thr Leu Leu Ile Gln Gln Phe Ala Val Asn Leu Lys Leu
145                 150                 155                 160
Phe Pro Ala Ala Thr Trp Thr Ser Pro Ile His Met Val Leu Pro Thr
                165                 170                 175
Ala Ala Leu Ala Val Gly Pro Met Ala Ile Ala Arg Leu Thr Arg
                180                 185                 190
Ser Ser Met Val Glu Val Leu Thr Gln Asp Tyr Ile Arg Thr Ala Lys
                195                 200                 205
Ala Lys Gly Leu Ser Pro Phe Lys Ile Ile Val Lys His Ala Leu Arg
    210                 215                 220
Asn Ala Leu Met Pro Val Ile Thr Val Leu Gly Thr Leu Val Ala Ser
225                 230                 235                 240
Ile Leu Thr Gly Ser Phe Val Ile Glu Lys Ile Phe Ala Ile Pro Gly
                245                 250                 255
Met Gly Lys Tyr Phe Val Glu Ser Ile Asn Gln Arg Asp Tyr Pro Val
                260                 265                 270
Ile Met Gly Thr Thr Val Phe Tyr Ser Val Ile Leu Ile Ile Met Leu
                275                 280                 285
Phe Leu Val Asp Leu Ala Tyr Gly Leu Leu Asp Pro Arg Ile Lys Leu
    290                 295                 300
His Lys Lys Gly
305

<210> SEQ ID NO 4
<211> LENGTH: 320
<212> TYPE: PRT
<213> ORGANISM: Artificial Sequence
<220> FEATURE:
<223> OTHER INFORMATION: amino acid sequence for dciAC

<400> SEQUENCE: 4

Met Asn Leu Pro Val Gln Thr Asp Glu Arg Gln Pro Glu Gln His Asn
 1                  5                  10                  15
Gln Val Pro Asp Glu Trp Phe Val Leu Asn Gln Glu Lys Asn Arg Glu
                20                  25                  30
Ala Asp Ser Val Lys Arg Pro Ser Leu Ser Tyr Thr Gln Asp Ala Trp
            35                  40                  45
Arg Arg Leu Lys Lys Asn Lys Leu Ala Met Ala Gly Leu Phe Ile Leu
    50                  55                  60
Leu Phe Leu Phe Val Met Ala Val Ile Gly Pro Phe Leu Ser Pro His
65                  70                  75                  80
Ser Val Val Arg Gln Ser Leu Thr Glu Gln Asn Leu Pro Pro Ser Ala
                85                  90                  95
Asp His Trp Phe Gly Thr Asp Glu Leu Gly Arg Asp Val Phe Thr Arg
            100                 105                 110
Thr Trp Tyr Gly Ala Arg Ile Ser Leu Phe Val Gly Val Met Ala Ala
        115                 120                 125
Leu Ile Asp Phe Leu Ile Gly Val Ile Tyr Gly Gly Val Ala Gly Tyr
    130                 135                 140
Lys Gly Gly Arg Ile Asp Ser Ile Met Met Arg Ile Ile Glu Val Leu
145                 150                 155                 160
Tyr Gly Leu Pro Tyr Leu Leu Val Val Ile Leu Leu Met Val Leu Met
                165                 170                 175
```

```
Gly Pro Gly Leu Gly Thr Ile Ile Val Ala Leu Thr Val Thr Gly Trp
            180                 185                 190

Val Gly Met Ala Arg Ile Val Arg Gly Gln Val Leu Gln Ile Lys Asn
        195                 200                 205

Tyr Glu Tyr Val Leu Ala Ser Lys Thr Phe Gly Ala Lys Thr Phe Arg
    210                 215                 220

Ile Ile Arg Lys Asn Leu Leu Arg Asn Thr Met Gly Ala Ile Ile Val
225                 230                 235                 240

Gln Met Thr Leu Thr Val Pro Ala Ala Ile Phe Ala Glu Ser Phe Leu
                245                 250                 255

Ser Phe Leu Gly Leu Gly Ile Gln Ala Pro Phe Ala Ser Trp Gly Val
            260                 265                 270

Met Ala Asn Asp Gly Leu Pro Thr Ile Leu Ser Gly His Trp Trp Arg
        275                 280                 285

Leu Phe Phe Pro Ala Phe Phe Ile Ser Ser Thr Met Tyr Ala Phe Asn
    290                 295                 300

Val Leu Gly Asp Gly Leu Gln Asp Ala Leu Asp Pro Lys Leu Arg Arg
305                 310                 315                 320
```

<210> SEQ ID NO 5
<211> LENGTH: 335
<212> TYPE: PRT
<213> ORGANISM: Artificial Sequence
<220> FEATURE:
<223> OTHER INFORMATION: amino acid sequence for dciAD

<400> SEQUENCE: 5

```
Met Glu Lys Val Leu Ser Val Gln Asn Leu His Val Ser Phe Thr Thr
1               5                   10                  15

Tyr Gly Gly Thr Val Gln Ala Val Arg Gly Val Ser Phe Asp Leu Tyr
            20                  25                  30

Lys Gly Glu Thr Phe Ala Ile Val Gly Glu Ser Gly Cys Gly Lys Ser
        35                  40                  45

Val Thr Ser Gln Ser Ile Met Gly Leu Leu Pro Pro Tyr Ser Ala Lys
    50                  55                  60

Val Thr Asp Gly Arg Ile Leu Phe Lys Asn Lys Asp Leu Cys Arg Leu
65                  70                  75                  80

Ser Asp Lys Glu Met Arg Gly Ile Arg Gly Ala Asp Ile Ser Met Ile
                85                  90                  95

Phe Gln Asp Pro Met Thr Ala Leu Asn Pro Thr Leu Thr Val Gly Asp
            100                 105                 110

Gln Leu Gly Glu Ala Leu Leu Arg His Lys Lys Met Ser Lys Lys Ala
        115                 120                 125

Ala Arg Lys Glu Val Leu Ser Met Leu Ser Leu Val Gly Ile Pro Asp
    130                 135                 140

Pro Gly Glu Arg Leu Lys Gln Tyr Pro His Gln Phe Ser Gly Gly Met
145                 150                 155                 160

Arg Gln Arg Ile Val Ile Ala Met Ala Leu Ile Cys Glu Pro Asp Ile
                165                 170                 175

Leu Ile Ala Asp Glu Pro Thr Thr Ala Leu Asp Val Thr Ile Gln Ala
            180                 185                 190

Gln Ile Leu Glu Leu Phe Lys Glu Ile Gln Arg Lys Thr Asp Val Ser
        195                 200                 205

Val Ile Leu Ile Thr His Asp Leu Gly Val Val Ala Gln Val Ala Asp
    210                 215                 220
```

```
Arg Val Ala Val Met Tyr Ala Gly Lys Met Ala Glu Ile Gly Thr Arg
225                 230                 235                 240

Lys Asp Ile Phe Tyr Gln Pro Gln His Pro Tyr Thr Lys Gly Leu Leu
                245                 250                 255

Gly Ser Val Pro Arg Leu Asp Leu Asn Gly Ala Glu Leu Thr Pro Ile
                260                 265                 270

Asp Gly Thr Pro Pro Asp Leu Phe Ser Pro Pro Gly Cys Pro Phe
                275                 280                 285

Ala Ala Arg Cys Pro Asn Arg Met Val Val Cys Asp Arg Val Tyr Pro
        290                 295                 300

Gly Gln Thr Ile Arg Ser Asp Ser His Thr Val Asn Cys Trp Leu Gln
305                 310                 315                 320

Asp Gln Arg Ala Glu His Ala Val Leu Ser Gly Asp Ala Lys Asp
                325                 330                 335

<210> SEQ ID NO 6
<211> LENGTH: 543
<212> TYPE: PRT
<213> ORGANISM: Artificial Sequence
<220> FEATURE:
<223> OTHER INFORMATION: amino acid sequence for dciAE

<400> SEQUENCE: 6

Met Lys Arg Val Lys Lys Leu Trp Gly Met Gly Leu Ala Leu Gly Leu
1               5                   10                  15

Ser Phe Ala Leu Met Gly Cys Thr Ala Asn Glu Gln Ala Gly Lys Glu
                20                  25                  30

Gly Ser His Asp Lys Ala Lys Thr Ser Gly Glu Lys Val Leu Tyr Val
            35                  40                  45

Asn Asn Glu Asn Glu Pro Thr Ser Phe Asp Pro Pro Ile Gly Phe Asn
50                  55                  60

Asn Val Ser Trp Gln Pro Leu Asn Asn Ile Met Glu Gly Leu Thr Arg
65                  70                  75                  80

Leu Gly Lys Asp His Glu Pro Glu Pro Ala Met Ala Glu Lys Trp Ser
                85                  90                  95

Val Ser Lys Asp Asn Lys Thr Tyr Thr Phe Thr Ile Arg Glu Asn Ala
                100                 105                 110

Lys Trp Thr Asn Gly Asp Pro Val Thr Ala Gly Asp Phe Glu Tyr Ala
            115                 120                 125

Trp Lys Arg Met Leu Asp Pro Lys Lys Gly Ala Ser Ser Ala Phe Leu
130                 135                 140

Gly Tyr Phe Ile Glu Gly Gly Glu Ala Tyr Asn Ser Gly Lys Gly Lys
145                 150                 155                 160

Lys Asp Asp Val Lys Val Thr Ala Lys Asp Asp Arg Thr Leu Glu Val
                165                 170                 175

Thr Leu Glu Ala Pro Gln Lys Tyr Phe Leu Ser Val Val Ser Asn Pro
                180                 185                 190

Ala Tyr Phe Pro Val Asn Glu Lys Val Asp Lys Asp Asn Pro Lys Trp
            195                 200                 205

Phe Ala Glu Ser Asp Thr Phe Val Gly Asn Gly Pro Phe Lys Leu Thr
210                 215                 220

Glu Trp Lys His Asp Asp Ser Ile Thr Met Glu Lys Ser Asp Thr Tyr
225                 230                 235                 240

Trp Asp Lys Asp Thr Val Lys Leu Asp Lys Val Lys Trp Ala Met Val
                245                 250                 255
```

```
Ser Asp Arg Asn Thr Asp Tyr Gln Met Phe Gln Ser Gly Glu Leu Asp
            260                 265                 270

Thr Ala Tyr Val Pro Ala Glu Leu Ser Asp Gln Leu Leu Asp Gln Asp
            275                 280                 285

Asn Val Asn Ile Val Asp Gln Ala Gly Leu Tyr Phe Tyr Arg Phe Asn
            290                 295                 300

Val Asn Met Glu Pro Phe Gln Asn Glu Asn Ile Arg Lys Ala Phe Ala
305                 310                 315                 320

Met Ala Val Asp Gln Glu Ile Val Lys Tyr Val Thr Lys Asn Asn
                325                 330                 335

Glu Lys Pro Ala His Ala Phe Val Ser Pro Gly Phe Thr Gln Pro Asp
            340                 345                 350

Gly Lys Asp Phe Arg Glu Ala Gly Gly Asp Leu Ile Lys Pro Asn Glu
            355                 360                 365

Ser Lys Ala Lys Gln Leu Leu Glu Lys Gly Met Lys Glu Glu Asn Tyr
            370                 375                 380

Asn Lys Leu Pro Ala Ile Thr Leu Thr Tyr Ser Thr Lys Pro Glu His
385                 390                 395                 400

Lys Lys Ile Ala Glu Ala Ile Gln Gln Lys Leu Lys Asn Ser Leu Gly
            405                 410                 415

Val Asp Val Lys Leu Ala Asn Met Glu Trp Asn Val Phe Leu Glu Asp
            420                 425                 430

Gln Lys Ala Leu Lys Phe Gln Phe Ser Gln Ser Ser Phe Leu Pro Asp
            435                 440                 445

Tyr Ala Asp Pro Ile Ser Phe Leu Glu Ala Phe Gln Thr Gly Asn Ser
            450                 455                 460

Met Asn Arg Thr Gly Trp Ala Asn Lys Glu Tyr Asp Gln Leu Ile Lys
465                 470                 475                 480

Gln Ala Lys Asn Glu Ala Asp Glu Lys Thr Arg Phe Ser Leu Met His
                485                 490                 495

Gln Ala Glu Glu Leu Leu Ile Asn Glu Ala Pro Ile Ile Pro Val Tyr
            500                 505                 510

Phe Tyr Asn Gln Val His Leu Gln Asn Glu Gln Val Lys Gly Ile Val
            515                 520                 525

Arg His Pro Val Gly Tyr Ile Asp Leu Lys Trp Ala Asp Lys Asn
            530                 535                 540
```

<210> SEQ ID NO 7
<211> LENGTH: 7
<212> TYPE: RNA
<213> ORGANISM: Artificial Sequence
<220> FEATURE:
<223> OTHER INFORMATION: putative Rnase cleavage site in subtilisin

<400> SEQUENCE: 7 acagaau                                                              7

<210> SEQ ID NO 8
<211> LENGTH: 7
<212> TYPE: RNA
<213> ORGANISM: Artificial Sequence
<220> FEATURE:
<223> OTHER INFORMATION: putative Rnase cleavage site in RNA I

<400> SEQUENCE: 8 acaguau                                                              7

```
<210> SEQ ID NO 9
<211> LENGTH: 7
<212> TYPE: RNA
<213> ORGANISM: Artificial Sequence
<220> FEATURE:
<223> OTHER INFORMATION: putative Rnase cleavage site in 9S RNA

<400> SEQUENCE: 9 acagaau                                                                    7

<210> SEQ ID NO 10
<211> LENGTH: 52
<212> TYPE: DNA
<213> ORGANISM: Artificial Sequence
<220> FEATURE:
<223> OTHER INFORMATION: primer

<400> SEQUENCE: 10
gcgcgcggat cccgtctgaa tgaattgtta tcggttttca gccgtgtacg gg                 52

<210> SEQ ID NO 11
<211> LENGTH: 52
<212> TYPE: DNA
<213> ORGANISM: Artificial Sequence
<220> FEATURE:
<223> OTHER INFORMATION: primer

<400> SEQUENCE: 11
gcgcgcctgc agcgggatgg agatgccgag tactgcaaga ctcatcgcgg cg                 52

<210> SEQ ID NO 12
<211> LENGTH: 45
<212> TYPE: DNA
<213> ORGANISM: Artificial Sequence
<220> FEATURE:
<223> OTHER INFORMATION: primer

<400> SEQUENCE: 12
gcgcgcgtcg acccatatct actgacatgt acaatttcat aacgc                        45

<210> SEQ ID NO 13
<211> LENGTH: 46
<212> TYPE: DNA
<213> ORGANISM: Artificial Sequence
<220> FEATURE:
<223> OTHER INFORMATION: primer

<400> SEQUENCE: 13
gcgcgcgtcg acgccgctca caccgcctga caggccagtt ctgagc                       46

<210> SEQ ID NO 14
<211> LENGTH: 37
<212> TYPE: DNA
<213> ORGANISM: Artificial Sequence
<220> FEATURE:
<223> OTHER INFORMATION: primer

<400> SEQUENCE: 14
gcgcgcggat ccgatgtgtc tgtcattctg attacgc                                 37

<210> SEQ ID NO 15
<211> LENGTH: 36
<212> TYPE: DNA
<213> ORGANISM: Artificial Sequence
<220> FEATURE:
<223> OTHER INFORMATION: primer
```

```
<400> SEQUENCE: 15
gcgcgcgtcg acgatcggcg gatcgaatga agtcgg                               36

<210> SEQ ID NO 16
<211> LENGTH: 38
<212> TYPE: DNA
<213> ORGANISM: Artificial Sequence
<220> FEATURE:
<223> OTHER INFORMATION: primer

<400> SEQUENCE: 16
gcgcgcgtcg acccaataaa gaatacgatc agctgatc                             38

<210> SEQ ID NO 17
<211> LENGTH: 36
<212> TYPE: DNA
<213> ORGANISM: Artificial Sequence
<220> FEATURE:
<223> OTHER INFORMATION: primer

<400> SEQUENCE: 17
gcgcgcctgc agtgtcccaa aacccccgat gcgcac                               36
```